US011596343B2

(12) United States Patent
Dai et al.

(10) Patent No.: US 11,596,343 B2
(45) Date of Patent: Mar. 7, 2023

(54) METHOD FOR ANALYZING ARRHYTHMIA IN REAL TIME, ELECTROCARDIOGRAM MONITORING DEVICE AND STORAGE MEDIUM

(71) Applicants: SHENZHEN MINDRAY BIO-MEDICAL ELECTRONICS CO., LTD., Shenzhen (CN); Shenzhen Mindray Scientific Co., Ltd., Shenzhen (CN)

(72) Inventors: Jian Dai, Shenzhen (CN); Pengfei Zuo, Shenzhen (CN); Wenyu Ye, Shenzhen (CN); Zehong Guan, Shenzhen (CN); Ming Li, Shenzhen (CN)

(73) Assignees: SHENZHEN MINDRAY BIOMEDICAL ELECTRONICS CO., LTD., Shenzhen (CN); Shenzhen Mindray Scientific Co., Ltd.

( * ) Notice: Subject to any disclaimer, the term of this patent is extended or adjusted under 35 U.S.C. 154(b) by 198 days.

(21) Appl. No.: 16/963,211

(22) PCT Filed: Jan. 18, 2018

(86) PCT No.: PCT/CN2018/073252
§ 371 (c)(1),
(2) Date: Jul. 18, 2020

(87) PCT Pub. No.: WO2019/140604
PCT Pub. Date: Jul. 25, 2019

(65) Prior Publication Data
US 2021/0128048 A1 May 6, 2021

(51) Int. Cl.
*A61B 5/35* (2021.01)
*G16H 40/63* (2018.01)
(Continued)

(52) U.S. Cl.
CPC .............. *A61B 5/35* (2021.01); *A61B 5/333* (2021.01); *A61B 5/339* (2021.01); *A61B 5/7221* (2013.01);
(Continued)

(58) Field of Classification Search
None
See application file for complete search history.

(56) References Cited

U.S. PATENT DOCUMENTS

| 4,023,564 A * | 5/1977 | Valiquette | A61B 5/35 600/521 |
| 4,721,114 A * | 1/1988 | Du | A61B 5/35 600/509 |

(Continued)

FOREIGN PATENT DOCUMENTS

| CN | 102835954 A | 12/2012 |
| CN | 103705234 A | 4/2014 |

(Continued)

OTHER PUBLICATIONS

Extended European Search Report issued in related European Application No. 18901214.9, dated Jan. 15, 2021, 8 pages.
(Continued)

*Primary Examiner* — Kennedy Schaetzle
(74) *Attorney, Agent, or Firm* — Bayes PLLC

(57) ABSTRACT

A method for analyzing arrhythmia in real time and an electrocardiogram monitoring device is disclosed. The method for analyzing arrhythmia in real time includes: acquiring a QRS template set currently used for arrhythmia analysis; determining whether each QRS template in the QRS template set is reliable; displaying information of a QRS template when the QRS template set contains an unreliable QRS template; determining the QRS template set according to an operation performed by a user on the
(Continued)

information of the QRS template; and acquiring real-time electrocardiogram data, performing arrhythmia analysis on the real-time electrocardiogram data by using a determined QRS template set, and outputting an arrhythmia analysis result of the real-time electrocardiogram data in real time. The method for analyzing arrhythmia in real time may achieve the correction of a template of a special waveform by means of editing a currently created QRS template. When the same type of waveform is analyzed again, a correct arrhythmia analysis result may be provided, which may improve the accuracy of arrhythmia analysis and improve the quality of electrocardiogram monitoring.

23 Claims, 7 Drawing Sheets

(51) Int. Cl.
*A61B 5/339* (2021.01)
*A61B 5/333* (2021.01)
*A61B 5/00* (2006.01)
*A61B 5/363* (2021.01)

(52) U.S. Cl.
CPC ............ *A61B 5/746* (2013.01); *G16H 40/63* (2018.01); *A61B 5/363* (2021.01)

(56) References Cited

U.S. PATENT DOCUMENTS

| | | | |
|---|---|---|---|
| 5,092,340 A | 3/1992 | Yamaguchi et al. | |
| 5,634,468 A | 6/1997 | Platt et al. | |
| 2002/0193695 A1* | 12/2002 | Koyrakh | A61B 5/35 600/510 |
| 2003/0120164 A1* | 6/2003 | Nielsen | A61B 5/0535 600/513 |
| 2004/0127805 A1* | 7/2004 | MacAdam | A61B 5/283 600/515 |
| 2007/0276276 A1 | 11/2007 | Cao et al. | |
| 2009/0275850 A1* | 11/2009 | Mehendale | A61B 5/35 600/509 |
| 2016/0278659 A1 | 9/2016 | Kaib et al. | |

FOREIGN PATENT DOCUMENTS

| | | |
|---|---|---|
| CN | 104586383 A | 5/2015 |
| CN | 107205657 A | 9/2017 |
| WO | 2008065432 A1 | 6/2008 |

OTHER PUBLICATIONS

International Search Report issued in corresponding International Application No. PCT/CN2018/073252, dated Oct. 15, 2018, 4 pages.

* cited by examiner

METHOD FOR ANALYZING ARRHYTHMIA IN REAL TIME, ELECTROCARDIOGRAM MONITORING DEVICE AND STORAGE MEDIUM

CROSS-REFERENCE TO RELATED APPLICATIONS

This disclosure is a U.S. national phase application of Patent Cooperation Treaty Application No. PCT/CN2018/073252, filed on Jan. 18, 2018, the content of which is hereby incorporated by reference.

TECHNICAL FIELD

The present application relates to the technical field of medical devices, and in particular to a method for analyzing arrhythmia in real time, an electrocardiogram monitoring device and a computer-readable storage medium.

BACKGROUND

An arrhythmia real-time analysis function is the most important function for current clinical electrocardiogram monitoring, and a template matching method is mainly used in current arrhythmia analysis systems. In the method, by acquiring information of morphology, intervals, etc. of a QRS complex (which is a general designation of three continuous wave groups of Q waves, R waves and S waves in an electrocardiogram signal) of an electrocardiogram signal, a certain number of QRS complex templates are created to form a template set, and a heartbeat type (normal or abnormal) corresponding to each of the templates is determined. Next, the QRS complex is compared with all the templates one by one to find out a template with the morphology most similar to that of the QRS complex, the heartbeat type of which then is the heartbeat type of the QRS complex. Finally, arrhythmia analysis is performed based on a classification result of the QRS complexes.

However, this analysis method excessively relies on the accuracy of the template type. When a special electrocardiogram waveform with continuous ventricular heartbeats, etc. occurring in a template creation stage is to be analyzed, it is difficult to determine whether the template type indicates normal or abnormal, and if it is determined that the template type indicates normal, alarm omissions of ventricular tachycardia may be caused, and if it is determined that the template type indicates abnormal, a large quantity of false alarms may be caused.

SUMMARY OF THE DISCLOSURE

The present application provides a method for analyzing arrhythmia in real time, an electrocardiogram monitoring device and a computer-readable storage medium, by which a currently created QRS template may be edited to improve the accuracy of arrhythmia analysis.

In a first aspect, the present application provides a method for analyzing arrhythmia in real time. The method for analyzing arrhythmia in real time comprises:

acquiring a QRS template set currently used for arrhythmia analysis, wherein the current QRS template set comprises a plurality of QRS templates;

determining whether each QRS template in the current QRS template set is reliable;

displaying information of a QRS template when the current QRS template set contains an unreliable QRS template, wherein the information of the QRS template comprises a reliability determination result of the QRS template;

determining the QRS template set according to an operation performed by a user on the information of the QRS template; and acquiring real-time electrocardiogram data, performing arrhythmia analysis on the real-time electrocardiogram data by using the determined QRS template set, and outputting an arrhythmia analysis result of the real-time electrocardiogram data in real time.

In a second aspect, the present application provides an electrocardiogram monitoring device, which comprises a display screen, a processor, a memory, and a computer program stored in the memory, wherein the processor is configured to execute the computer program stored in the memory to carry out the steps of:

acquiring a QRS template set currently used for arrhythmia analysis, wherein the current QRS template set comprises a plurality of QRS templates;

determining whether each QRS template in the current QRS template set is reliable;

controlling the display screen to display information of a QRS template when the current QRS template set contains an unreliable QRS template, wherein the information of the QRS template comprises a reliability determination result of the QRS template;

determining the QRS template set according to an operation performed by a user on the information of the QRS template; and acquiring real-time electrocardiogram data, performing arrhythmia analysis on the real-time electrocardiogram data by using the determined QRS template set, and outputting an arrhythmia analysis result of the real-time electrocardiogram data in real time.

In a third aspect, the present application further provides a method for analyzing arrhythmia in real time. The method for analyzing arrhythmia in real time comprises:

acquiring a QRS template set currently used for arrhythmia analysis, wherein the current QRS template set comprises a plurality of QRS templates;

receiving a call operation, and calling information of a QRS template according to the received call operation;

determining the QRS template set according to an operation performed by a user on the information of the QRS template; and acquiring real-time electrocardiogram data, performing arrhythmia analysis on the real-time electrocardiogram data by using the determined QRS template set, and outputting an arrhythmia analysis result of the real-time electrocardiogram data in real time.

In a fourth aspect, the present application provides an electrocardiogram monitoring device, which comprises a processor, a memory, and a computer program stored in the memory. The processor is configured to execute the computer program stored in the memory to carry out the steps of:

acquiring a QRS template set currently used for arrhythmia analysis, wherein the current QRS template set comprises a plurality of QRS templates;

receiving a call operation, and calling information of a QRS template according to the received call operation;

determining the QRS template set according to an operation performed by a user on the information of the QRS template; and acquiring real-time electrocardiogram data, performing arrhythmia analysis on the real-time electrocardiogram data by using the determined QRS template set, and outputting an arrhythmia analysis result of the real-time electrocardiogram data in real time.

In a fifth aspect, the present application provides a computer-readable storage medium having computer instructions stored thereon, wherein the computer instructions implement, when executed by a processor, the steps of the method for analyzing arrhythmia in real time as described in any of the embodiments.

The method for analyzing arrhythmia in real time in the present invention may achieve the correction of a template of a special waveform by means of editing a currently created QRS template; when the same type of waveform is analyzed again, a correct arrhythmia analysis result may be provided, which may improve the accuracy of arrhythmia analysis and improve the quality of electrocardiogram monitoring.

BRIEF DESCRIPTION OF THE DRAWINGS

In order to more clearly illustrate technical solutions in the embodiments of the present application or in the prior art, a brief introduction to the accompanying drawings required for the description of the embodiments or the prior art will be provided below. Obviously, the accompanying drawings in the following description are only some of the embodiments of the present application, and those of ordinary skill in the art would also be able to derive other drawings from these drawings without making creative efforts.

DETAILED DESCRIPTION OF EMBODIMENTS

The technical solutions of embodiments of the present application will be described below clearly and comprehensively in conjunction with accompanying drawings of the embodiments of the present application. Apparently, the embodiments described are merely some of, rather than all of, the embodiments of the present application. Based on the embodiments of the present application, all other embodiments obtained by those of ordinary skill in the art without making creative efforts fall within the scope of protection of the present application.

Figure 1:
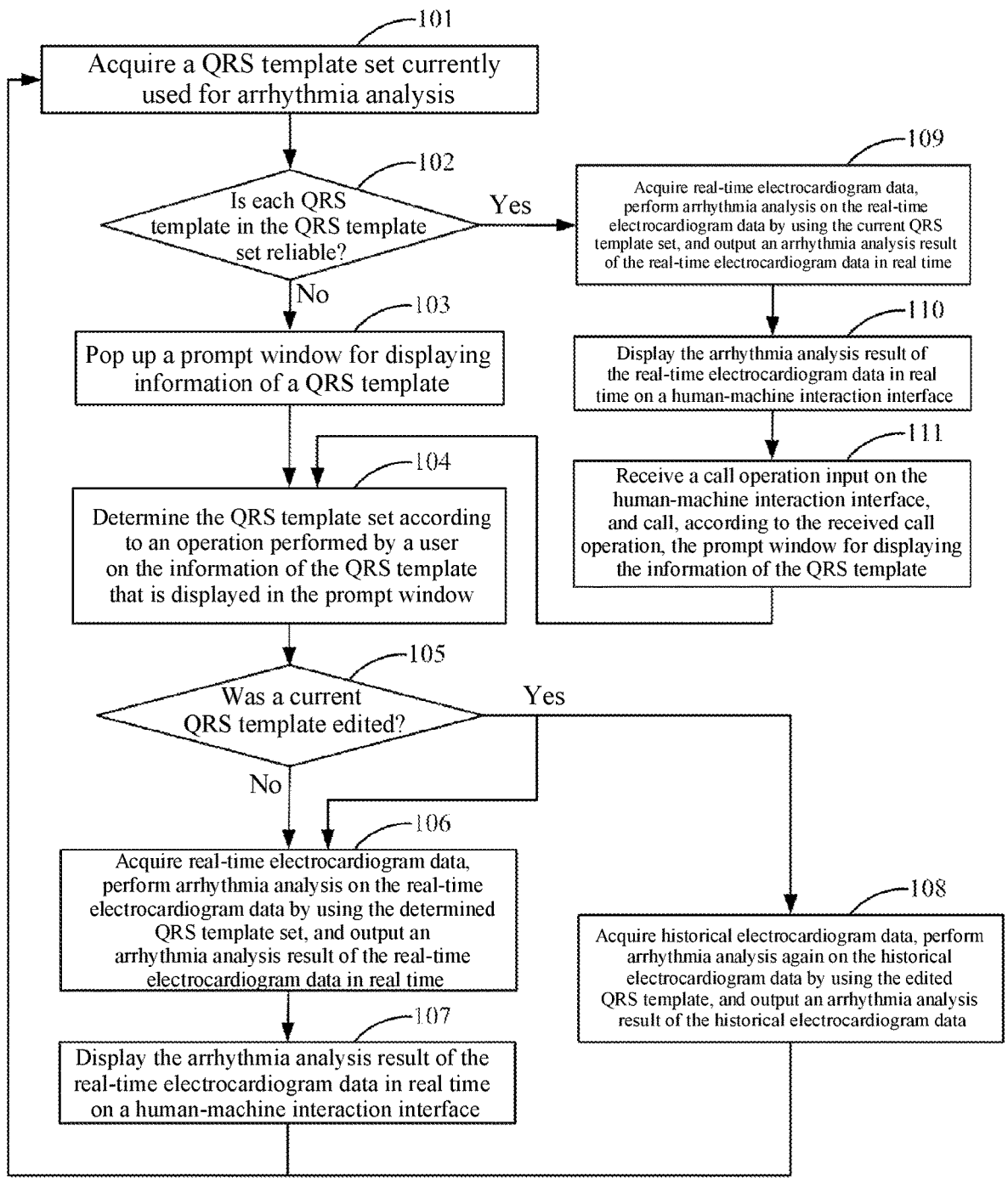
FIG. 1 is a schematic flowchart of a method for analyzing arrhythmia in real time, provided in an embodiment of the present application.

Referring to FIG. 1, it is a schematic flowchart of a method for analyzing arrhythmia in real time, provided in an embodiment of the present application, and the method for analyzing arrhythmia in real time is applied to an electrocardiogram monitoring device, such as an electrocardiogram detector. It should be noted that the method for analyzing arrhythmia in real time in the embodiment of the present application is not limited to the steps and order in the flowchart shown in FIG. 1. According to different requirements, a step may be added to or removed from the steps in the flowchart or the order of the steps may be changed.

As shown in FIG. 1, the method for analyzing arrhythmia in real time comprises the following steps:

step 101, acquiring a QRS template set currently used for arrhythmia analysis.

The current QRS template set comprises a plurality of created QRS templates, such as 5 to 6 QRS templates. It may be understood that each QRS template is created from one QRS complex, and the QRS complex may be a QRS complex directly acquired during a process of arrhythmia analysis or a certain QRS complex in historical electrocardiogram data.

Step 102, determining whether each QRS template in the current QRS template set is reliable. Step 103 is carried out if the current QRS template set contains an unreliable QRS template. Step 109 is carried out if each QRS template in the current QRS template set is reliable.

Step 103, popping up a prompt window for displaying information of a QRS template.

The information of the QRS template that is displayed on the prompt window is information of the QRS template in the current QRS template set, and the information of the QRS template comprises a reliability determination result of the QRS template.

In one embodiment, step 103 comprises: popping up two prompt windows, for displaying information of a reliable QRS template in one of the prompt windows and information of an unreliable QRS template in the other prompt window, according to the reliability determination result of each QRS template, namely, separately displaying the reliable QRS template and the unreliable QRS template in different prompt windows.

Optionally, in another embodiment, step 103 comprises: popping up one prompt window, for displaying information of an unreliable QRS template in the prompt window according to the reliability determination result of each QRS template.

Optionally, in another embodiment, step 103 comprises: popping up one prompt window, for displaying information of each QRS template in the prompt window, namely, displaying both a reliable QRS template and an unreliable QRS template in the one prompt window.

Step 104, determining the QRS template set according to an operation performed by a user on the information of the QRS template that is displayed in the prompt window.

The information of the current QRS template further comprises, but is not limited to, the type of the QRS template and morphological feature parameters of a QRS complex. The morphological feature parameters of the QRS complex comprise, but are not limited to, the amplitude, width and slope of the QRS complex, and a start point and an end point of the QRS complex.

Figure 2:
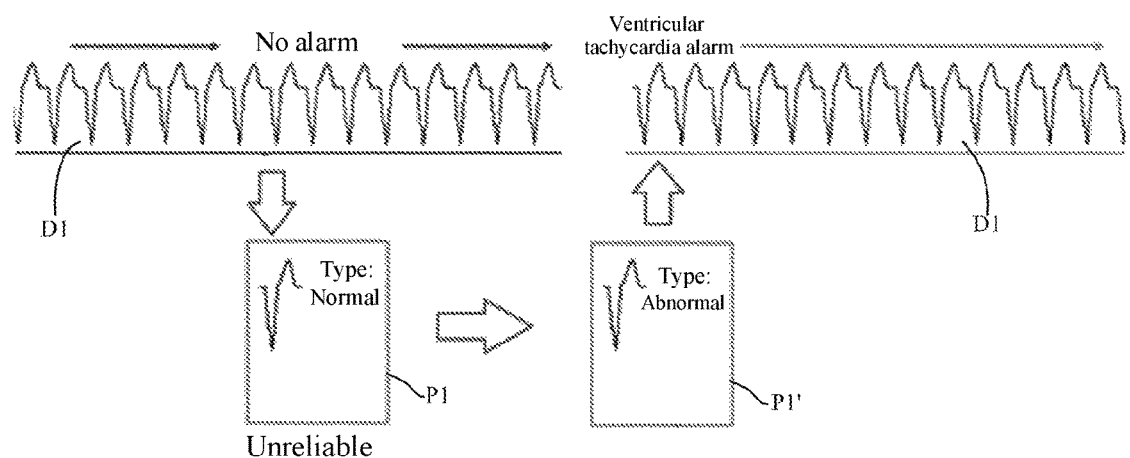
FIG. 2 is a schematic diagram of performing arrhythmia analysis on real-time electrocardiogram data, provided in an embodiment of the present application.
Figure 3:
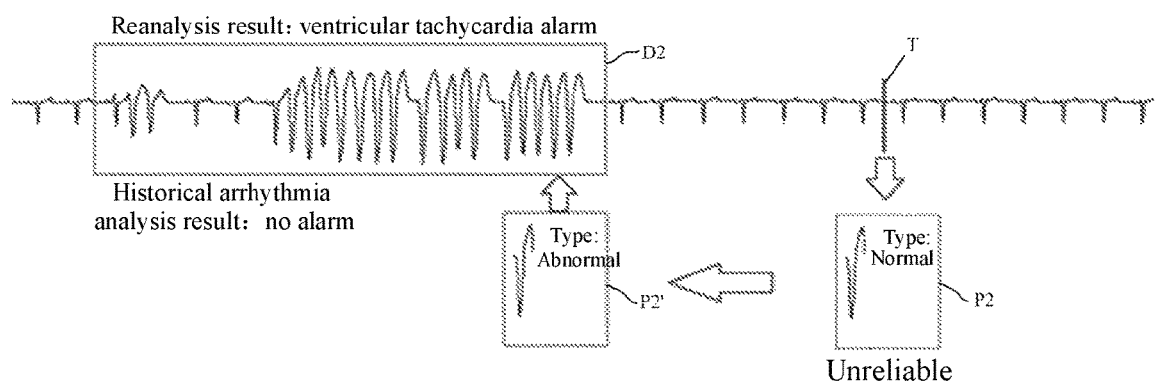
FIG. 3 is a schematic diagram of performing arrhythmia analysis on historical electrocardiogram data, provided in an embodiment of the present application.

During practical application, as shown in FIG. 2 or 3, the information of the currently created QRS templates may be simultaneously displayed by means of, but not limited to, a human-machine interaction interface. In this embodiment, the information of only one unreliable QRS template is displayed in both schematic diagrams of FIGS. 2 and 3.

In this embodiment, the reliability determination of a QRS template comprises automatic determination by a machine system and human determination. For example, on the basis of the system automatically determining the reliability of a certain QRS template, the medical personnel may further determine, according to actual clinical conditions and their own experience, whether the QRS template is reliable.

In this embodiment, the operation performed by the user on the information of the QRS template comprises an editing operation and a confirmation operation.

In this embodiment, said determining the QRS template set according to an operation performed by a user on the information of the QRS template that is displayed in the prompt window comprises:

determining a type of the operation performed by the user on the information of the QRS template;

updating, if the operation is an editing operation, information of a corresponding QRS template in the QRS template set according to the editing operation; and maintaining, if the operation is a confirmation operation, information of a corresponding QRS template in the QRS template set unchanged according to the confirmation operation.

It may be understood that the prompt window may be provided with an edition button and a confirmation button, such that the medical personnel may edit or confirm the currently displayed information of the QRS template in the prompt window by means of the edition or confirmation button. The operation performed by the user on the information of the QRS template may be a click operation on the confirmation button or on the edition button and an editing operation for further input following the clicking of the edition button, performed by the user such as the medical personnel in the prompt window.

It may be understood that if it is displayed in the prompt window that the system determines that a certain QRS template is unreliable whereas the medical personnel determines that the QRS template is reliable, that is to say, when considering it unnecessary to perform an editing operation of modifying the QRS template, etc., the medical personnel may confirm information of the QRS template by means of, for example, clicking the confirmation button in the prompt window, so as to maintain the original information of the QRS template unchanged.

In addition, if it is displayed in the prompt window that the system determines that a certain QRS template is unreliable and the medical personnel also determines that the QRS template is unreliable, that is to say, when considering it necessary to perform an editing operation of modifying the QRS template, etc., the medical personnel may edit information of the QRS template by means of, for example, clicking the edition button in the prompt window, so as to modify the information of the QRS template. The content for edition comprises, but is not limited to, modification to the type of the QRS template and morphological feature parameters of the QRS complex, such as parameters of the amplitude, the width and the slope of the QRS complex, and a start point and an end point of the QRS complex.

In other embodiments, the content for edition may further comprise replacement of the QRS template, for example, deleting an original QRS template, and then setting a new QRS template.

It may be understood that after step 104, the method for analyzing arrhythmia in real time may further comprise: saving the edited or confirmed QRS template.

Step 105, determining whether a current QRS template was edited. Steps 106 and 108 are separately carried out if the current QRS template was edited. Step 106 is carried out if the current QRS template has not been edited.

Step 106, acquiring real-time electrocardiogram data, performing arrhythmia analysis on the real-time electrocardiogram data by using the determined QRS template set, and outputting an arrhythmia analysis result of the real-time electrocardiogram data in real time.

Specifically, as shown in FIG. 2, during the process of analyzing arrhythmia in real time, the type of one QRS template P1 in the current template set is a type Normal. If it is determined in step 102 above that the QRS template P1 is unreliable, the medical personnel may modify the type of the QRS template P1 to a type Abnormal in the popped-up prompt window, so as to obtain an edited QRS template P1', and perform arrhythmia analysis on real-time electrocardiogram data D1 by using a QRS template set containing the edited QRS template P1'.

As shown in FIG. 2, when arrhythmia analysis is performed on the real-time electrocardiogram data D1 by using the QRS template P1 before edition, an analysis result indicates no alarm, that is to say, the real-time electrocardiogram data D1 is analyzed to be of a normal rhythm, but in fact, the real-time electrocardiogram data D1 should be of an abnormal rhythm. When arrhythmia analysis is performed on the real-time electrocardiogram data D1 by using the edited QRS template P1', an analysis result obtained indicates a ventricular tachycardia alarm.

It may be understood that under general conditions, creating a QRS template from electrocardiogram waveform parameters, and analyzing the type of arrhythmia by means of a template matching method may meet requirements of real-time analysis of arrhythmia in most cases. But when a special electrocardiogram waveform is encountered or there is a doubt on the type of a current template, for example, when an abnormal electrocardiogram waveform occurs and an arrhythmia analysis result deviates from the actual situation, as described above, each QRS template in the QRS template set may be edited or confirmed so as to reduce the misclassification of QRS complexes and correct the arrhythmia analysis result, thereby improving the accuracy of the real-time analysis result of arrhythmia.

Step 107, displaying the arrhythmia analysis result of the real-time electrocardiogram data in real time on a human-machine interaction interface. The flow returns to step 101.

In this embodiment, after step 107, the method for analyzing arrhythmia in real time may further comprise: outputting, when the arrhythmia analysis result of the real-time electrocardiogram data indicates an abnormal rhythm, a real-time alarm prompt about the abnormal rhythm.

When the current arrhythmia analysis result of the real-time electrocardiogram data indicates an abnormal rhythm, a real-time alarm prompt about the abnormal rhythm is output to warn the medical personnel, wherein the content of the alarm prompt may comprise the specific type of arrhythmia.

It may be understood that a display screen of the electrocardiogram monitoring device can be used to provide the human-machine interface, and an alarm apparatus on the electrocardiogram monitoring device can be used to output the real-time alarm prompt.

Step 108, acquiring historical electrocardiogram data, performing arrhythmia analysis again on the historical electrocardiogram data by using the edited QRS template, and outputting an arrhythmia analysis result of the historical electrocardiogram data. The flow returns to step 101.

Specifically, as shown in FIG. 3, during the process of analyzing arrhythmia in real time, for example, by way of taking a moment T as a real-time analysis time point, the type of one QRS template P2 in the current template set is a type Normal. If it is determined in step 102 above that the QRS template P2 is unreliable, the medical personnel may modify the type of the template P2 to a type Abnormal in the popped-up prompt window, so as to obtain an edited QRS template P2', and perform arrhythmia analysis again on the historical electrocardiogram data D2 by using a QRS template set containing the edited QRS template P2'.

As shown in FIG. 3, a historical arrhythmia analysis result of the historical electrocardiogram data D2 indicates no alarm, that is to say, during the process of historical arrhythmia analysis, the historical electrocardiogram data D2 is analyzed to be of a normal rhythm, but in fact, the historical electrocardiogram data D2 should be of an abnormal rhythm. After arrhythmia analysis is performed again on the historical electrocardiogram data D2 by using the edited QRS template P2', a reanalysis result obtained indicates a ventricular tachycardia alarm.

Step 109, acquiring real-time electrocardiogram data, performing arrhythmia analysis on the real-time electrocardiogram data by using the current QRS template set, and outputting an arrhythmia analysis result of the real-time electrocardiogram data in real time.

Step 110, displaying the arrhythmia analysis result of the real-time electrocardiogram data in real time on a human-machine interaction interface.

As described above, in this embodiment, after step 110, the method for analyzing arrhythmia in real time may further comprise: outputting, when the arrhythmia analysis result of the real-time electrocardiogram data indicates an abnormal rhythm, a real-time alarm prompt about the abnormal rhythm.

Step 111, receiving a call operation input on the human-machine interaction interface, and calling, according to the received call operation, the prompt window for displaying the information of the QRS template in the current QRS template set. The flow jumps to step 104 of determining the QRS template set according to the operation performed by the user on the information of the QRS template in the current QRS template set that is displayed in the prompt window.

As described above, the information of the QRS template that is displayed in the prompt window comprises a reliability determination result of the QRS template.

It may be understood that, in this embodiment, if it is determined by the system that all the QRS templates in the current QRS template set are reliable, the prompt window for displaying the information of the QRS template in the current QRS template set is not actively popped up.

As described above, on the basis of the system automatically determining the reliability of a certain QRS template, the medical personnel may further determine, according to actual clinical conditions and their own experience, whether the QRS template is reliable.

For example, during the analysis of a special electrocardiogram waveform, if determining, according to actual clinical conditions and their own experience, that the result of arrhythmia analysis with the currently created QRS template deviates from the actual situation, the medical personnel may click a relevant button on the human-machine interaction interface in real time to actively display the currently created QRS template, namely, calling the prompt window for displaying the information of the QRS template in the current QRS template set.

If determining that a certain QRS template is reliable, the medical personnel may input a confirmation operation in the prompt window so as to maintain the original information of the QRS template unchanged. In addition, if determining that the QRS template is unreliable, the medical personnel may input an editing operation in the prompt window so as to modify information of the QRS template, such as modifying the type, amplitude, width and slope of the QRS template, a start point and an end point of a QRS complex, etc.

The method for analyzing arrhythmia in real time in the present invention may achieve the correction of a template of a special waveform by means of editing a currently created QRS template; when the same type of waveform is analyzed again, a correct arrhythmia analysis result may be provided.

In addition, if the template is inaccurate, this may cause serious arrhythmia reflected in historical electrocardiogram data of a patient not to be recognized, which further has an effect on determination of the patient's condition by the medical personnel, thereby increasing medical risks, and lowering the quality of electrocardiogram monitoring. By means of the method for analyzing arrhythmia in real time of the present invention, the historical electrocardiogram data is reanalyzed by using the edited QRS template, such that omission of serious arrhythmia reflected in the historical electrocardiogram data of the patient may be avoided, and alarm omissions may be reduced, thereby improving the accuracy of arrhythmia analysis and then improving the quality of electrocardiogram monitoring.

Figure 4:
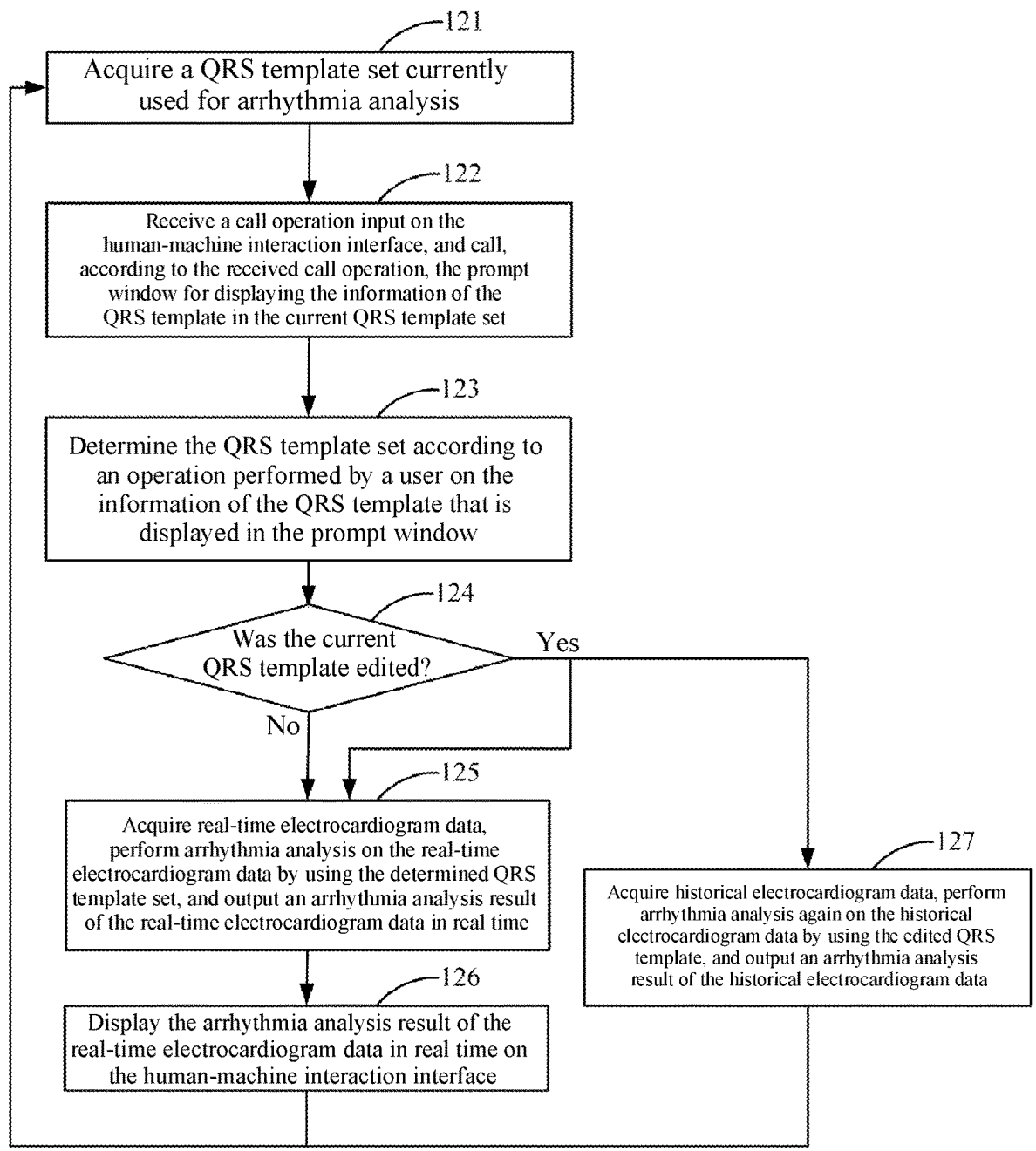
FIG. 4 is a schematic flowchart of another method for analyzing arrhythmia in real time, provided in an embodiment of the present application.

Referring to FIG. 4, it is a schematic flowchart of a method for analyzing arrhythmia in real time, provided in an embodiment of the present application, and the method for analyzing arrhythmia in real time is applied to an electrocardiogram monitoring device, such as an electrocardiogram detector. It should be noted that the method for analyzing arrhythmia in real time in the embodiment of the present application is not limited to the steps and order in the flowchart shown in FIG. 2. According to different requirements, a step may be added to or removed from the steps in the flowchart or the order of the steps may be changed.

As shown in FIG. 4, the method for analyzing arrhythmia in real time comprises the following steps:

step 121, acquiring a QRS template set currently used for arrhythmia analysis.

Step 122, receiving a call operation input on the human-machine interaction interface, and calling, according to the received call operation, the prompt window for displaying the information of the QRS template in the current QRS template set.

Specifically, specific technical details of steps 121 and 122 in this embodiment may respectively refer to specific introduction to relevant technical details of steps 101 and 111 in the embodiment of FIG. 1 of the present application, which will not be described here again for the sake of saving space and avoiding repetition.

As described above, the medical personnel may determine, according to actual clinical conditions and their own experience, whether the QRS template is reliable.

In one embodiment, the medical personnel may input, at any moment during the process of arrhythmia analysis, a call operation on the human-machine interaction interface to call the information of the QRS template in the current QRS template set, so as to determine whether the QRS template is reliable.

In another embodiment, before step 122, the method for analyzing arrhythmia in real time may further comprise the steps of:

acquiring real-time electrocardiogram data, performing arrhythmia analysis on the real-time electrocardiogram data by using the current QRS template set, and outputting an arrhythmia analysis result of the real-time electrocardiogram data in real time; and displaying the arrhythmia analysis result of the real-time electrocardiogram data in real time on a human-machine interaction interface.

In this way, when determining, according to actual clinical conditions and their own experience, that the result of arrhythmia analysis with the currently created QRS template deviates from the actual situation, the medical personnel may click a relevant button on the human-machine interaction interface in real time to actively display the currently created QRS template, namely, calling the prompt window for displaying the information of the QRS template in the current QRS template set.

Step 123, determining the QRS template set according to an operation performed by a user on the information of the QRS template that is displayed in the prompt window.

In this embodiment, the operation performed by the user on the information of the QRS template comprises an editing operation and a confirmation operation.

Step 124, determining whether a current QRS template was edited. Steps 125 and 127 are separately carried out if the current QRS template was edited. Step 125 is carried out if the current QRS template has not been edited.

Step 125, acquiring real-time electrocardiogram data, performing arrhythmia analysis on the real-time electrocardiogram data by using the determined QRS template set, and outputting an arrhythmia analysis result of the real-time electrocardiogram data in real time.

Step 126, displaying the arrhythmia analysis result of the real-time electrocardiogram data in real time on a human-machine interaction interface. The flow returns to step 121.

Step 127, acquiring historical electrocardiogram data, performing arrhythmia analysis again on the historical electrocardiogram data by using the edited QRS template, and outputting an arrhythmia analysis result of the historical electrocardiogram data. The flow returns to step 121.

Specifically, specific technical details of steps 123 to 127 in this embodiment may respectively refer to specific introduction to relevant technical details of steps 104 to 108 in the embodiment of FIG. 1 of the present application, which will not be described here again for the sake of saving space and avoiding repetition.

Figure 5:
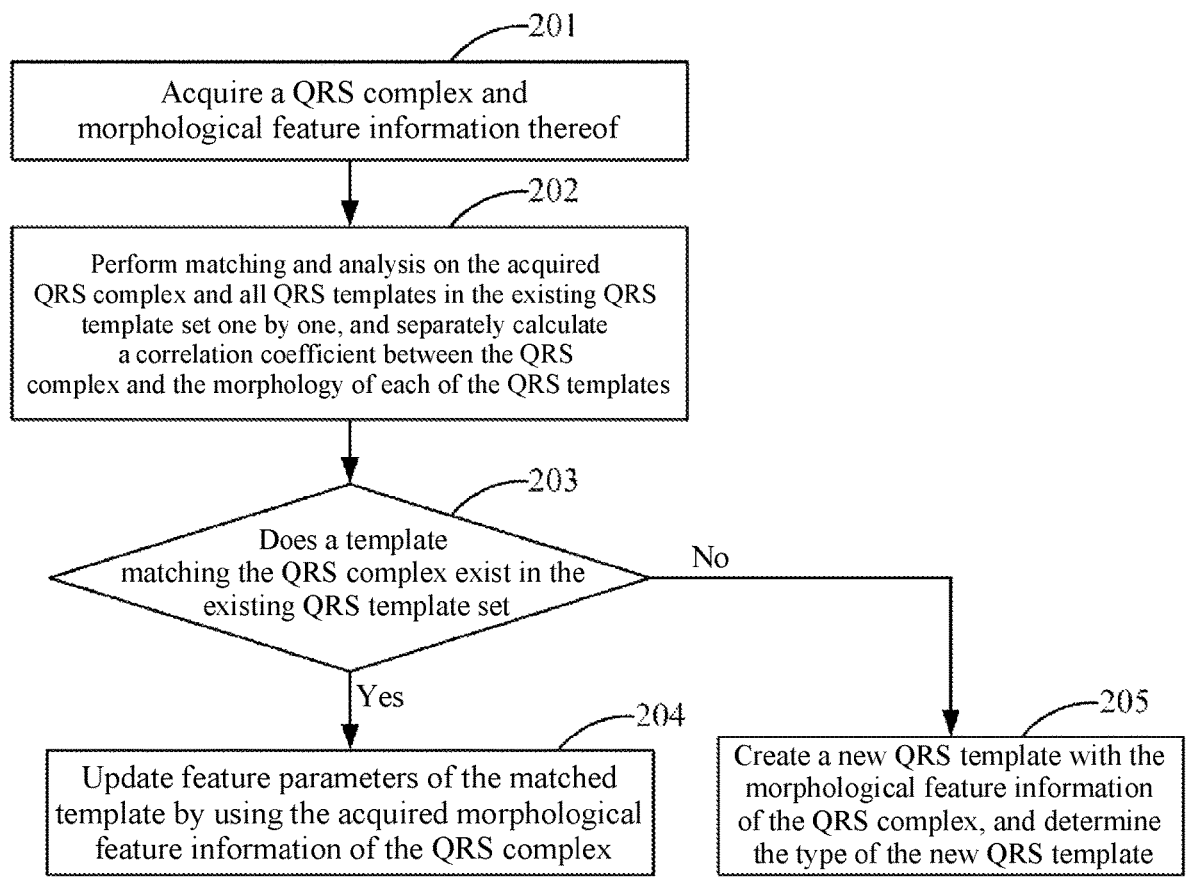
FIG. 5 is a schematic flowchart of a method for creating a QRS template, provided in an embodiment of the present application.

FIG. 5 is a schematic flowchart of a method for creating a QRS template, provided in an embodiment of the present application. The method for creating a QRS template comprises the following steps:

step 201, acquiring a QRS complex and morphological feature information thereof.

The QRS complex may be a QRS complex in real-time electrocardiogram data that is detected during the process of current arrhythmia analysis, or a certain QRS complex in historical electrocardiogram data. The morphological feature information of the QRS complex comprises, but is not limited to, the amplitude, width and slope of the QRS complex.

Step 202, matching on the acquired QRS complex and all QRS templates in the existing QRS template set one by one, and separately calculating a correlation coefficient between the QRS complex and the morphology of each of the QRS templates.

It may be understood that each QRS template in the existing QRS template set is a classified template. During matching, the morphological feature information of the QRS complex may be matched with feature parameters of each QRS template in the existing QRS template set, and the feature parameters of the QRS templates comprise, but are not limited to, the width, amplitude and slope of the QRS complex.

The value range of the correlation coefficient may be set arbitrarily. For example, the value range of the correlation coefficient may be set between plus and minus 100, wherein the greater the value is, the higher the similarity is.

Step 203, determining, according to each calculated correlation coefficient, whether a template matching the QRS complex exists in the existing QRS template set. Step 204 is carried out if a matched template matching the QRS complex exists in the existing QRS template set. Step 205 is carried out if no matched template matching the QRS complex exists in the existing QRS template set.

In this embodiment, a correlation threshold may be preset, for example, to 90. If the calculated correlation coefficient between the QRS complex and one of the QRS templates is greater than 90, it can be considered that the QRS complex matches the QRS template, otherwise, it can be considered that the QRS complex does not match the QRS template.

It may be understood that in step 203, a QRS template, which has the maximum correlation coefficient between same and the QRS complex that is greater than a preset correlation threshold, is selected as the optimal matched template for the QRS complex.

Step 204, updating feature parameters of the matched template by using the acquired morphological feature information of the QRS complex.

Step 205, creating a new QRS template with the morphological feature information of the QRS complex, and determining the type of the new QRS template, wherein the type comprises a type Normal and a type Abnormal.

It may be understood that the creation and updating of the QRS template are carried out in real time during the process of arrhythmia analysis, such that more morphological feature information of QRS complexes of the same type may be collected for the feature parameters of the created QRS template, for the determination of the reliability of the QRS template after a certain duration or after the collection of sufficient morphological feature information of the QRS complexes of same type. In addition, a new QRS template may be created for a newly emerging waveform, such that when the same type of waveform is analyzed again, the newly created QRS template may be used to analyze the same type of waveform.

Figure 6:
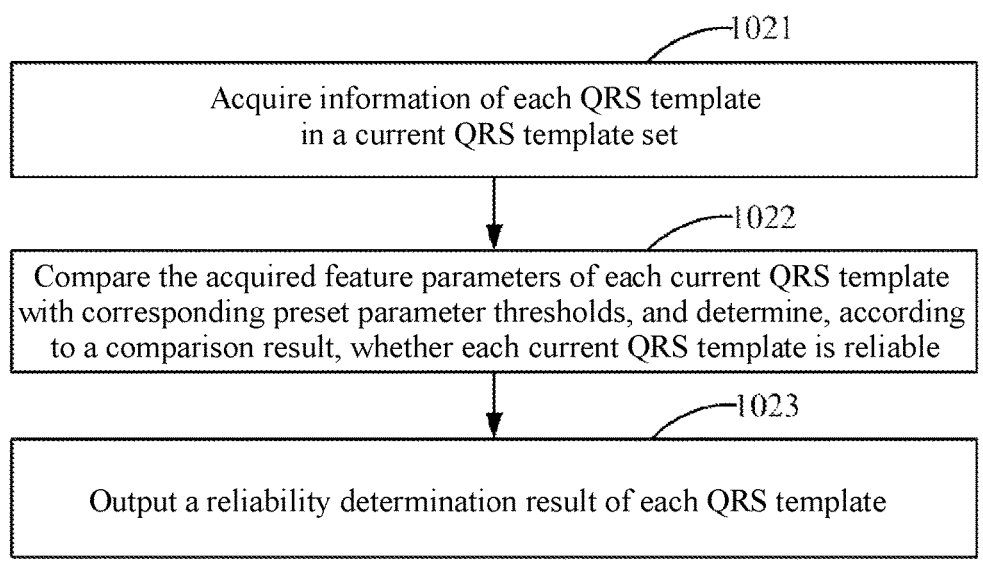
FIG. 6 is a detailed schematic flowchart of step 102 in FIG. 1.

Referring to FIG. 6, it is a detailed schematic flowchart of step 102 in FIG. 1. In this embodiment, step 102 comprises:

Step 1021, acquiring information of each QRS template in a current QRS template set.

The information of the QRS template further comprises the type and feature parameters of the QRS template. The feature parameters of the QRS template comprise, but is not limited to, the width, amplitude and slope of a QRS complex, and a start point and an end point of the QRS complex.

Step 1022, comparing the acquired feature parameters of each current QRS template with corresponding preset parameter thresholds, and determining, according to a comparison result, whether each current QRS template is reliable.

In one embodiment, it may be determined, depending on whether the feature parameters of the QRS template exceed the corresponding preset parameter thresholds, whether the current template is reliable.

It may be understood that QRS templates of different types also have different feature parameter thresholds.

The parameter thresholds may be set with reference to medically statistical normal values. For example, a QRS template of a type Normal may have a QRS width threshold that is set as 20 ms. A QRS template of a type Abnormal may have a QRS width threshold that is set as 120 ms. In one embodiment, if all or some feature parameters of a template of a certain type exceed the corresponding preset parameter thresholds and meet the corresponding determination conditions, it is determined that the QRS template is unreliable.

Step 1023, outputting a reliability determination result of each QRS template.

Figure 7:
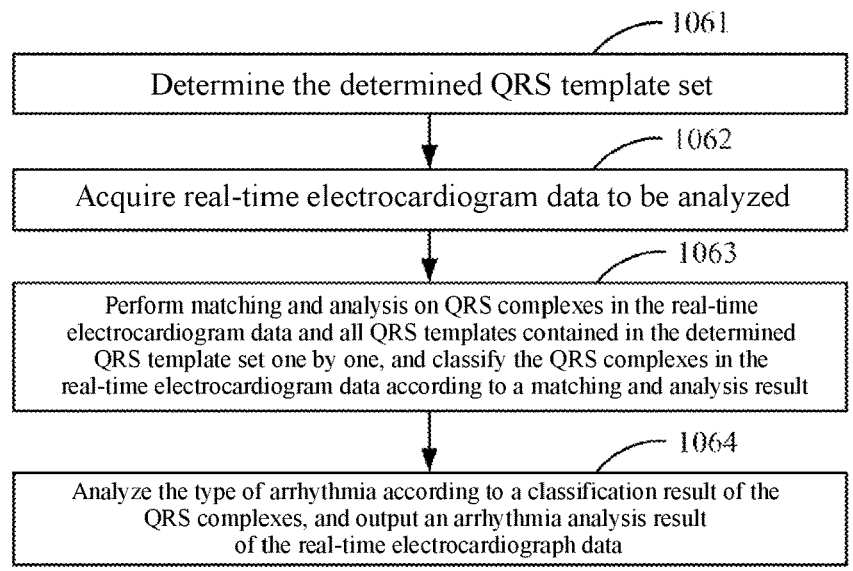
FIG. 7 is a detailed schematic flowchart of step 106 in FIG. 1 or step 125 in FIG. 4.

Referring to FIG. 7, it is a detailed schematic flowchart of step 106 in FIG. 1 or step 125 in FIG. 4. In this embodiment, step 106 or step 125 comprises:

step 1061, acquiring the determined QRS template set.

Step 1062, acquiring real-time electrocardiogram data to be analyzed.

Step 1063, matching QRS complexes in the real-time electrocardiogram data with all QRS templates contained in the determined QRS template set one by one, and classifying the QRS complexes in the real-time electrocardiogram data according to a matching result.

Specifically, step 1063 comprises:

matching the QRS complex in the real-time electrocardiogram data with all the QRS templates contained in the determined QRS template set one by one, and calculating a correlation coefficient between the QRS complex and the morphology of each of the QRS templates contained in the determined QRS template set; and determining, when there is a maximum correlation coefficient between the QRS complex and one of the QRS templates and the maximum correlation coefficient is greater than a preset correlation threshold, that the QRS complex matches the one of the QRS templates, and determining the type of the QRS complex according to the type of the one of the QRS templates, that is to say, classifying the QRS complex as the type of the one of the QRS templates.

Step 1064, analyzing the type of arrhythmia according to a classification result of the QRS complexes, and outputting an arrhythmia analysis result of the real-time electrocardiogram data.

In this embodiment, "analyzing the type of arrhythmia according to a classification result of the QRS complexes" comprises: analyzing, in combination with specific arrhythmia determination criteria and/or preset thresholds, the type of QRS complexes already classified within a certain duration, so as to determine the type of arrhythmia.

For example, if five continuous QRS complexes of a type Abnormal have occurred in succession at present, and a current heat rhythm value is greater than 120 bpm, it is determined that the type of arrhythmia indicates ventricular tachycardia. If all determination conditions for arrhythmia are not met, it is determined that a current electrocardiogram signal is of a normal rhythm.

Figure 8:
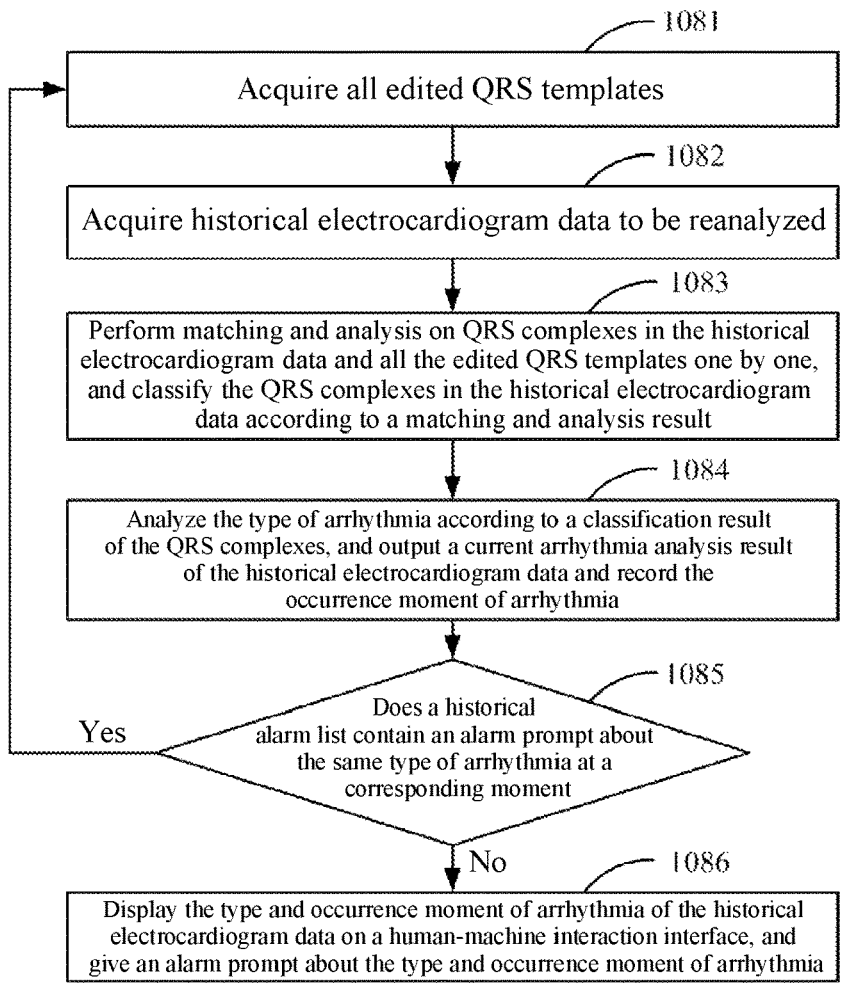
FIG. 8 is a detailed schematic flowchart of step 108 in FIG. 1 or step 127 in FIG. 4.

Referring to FIG. 8, it is a detailed schematic flowchart of step 108 in FIG. 1 or step 127 in FIG. 4. In this embodiment, step 108 comprises:

step 1081, acquiring all the edited QRS templates.

Step 1082, acquiring historical electrocardiogram data to be reanalyzed.

Step 1083, matching QRS complexes in the historical electrocardiogram data and all the edited QRS templates one by one, and classifying the QRS complexes in the historical electrocardiogram data according to a matching result.

Specifically, step 1083 comprises:

matching the QRS complex in the historical electrocardiogram data with all the edited QRS templates one by one, and calculating a correlation coefficient between the QRS complex and the morphology of each of the edited QRS templates; and determining, when there is a maximum correlation coefficient between the QRS complex and one of the QRS templates and the maximum correlation coefficient is greater than a preset correlation threshold, that the QRS complex matches the one of the QRS templates, and determining the type of the QRS complex according to the type of the one of the QRS templates, that is to say, classifying the QRS complex as the type of the one of the QRS templates.

Step 1084, analyzing the type of arrhythmia according to a classification result of the QRS complexes, and outputting a current arrhythmia analysis result of the historical electrocardiogram data and recording the occurrence moment of arrhythmia.

In this embodiment, "analyzing the type of arrhythmia according to a classification result of the QRS complexes" comprises: analyzing, in combination with specific arrhythmia determination criteria and/or preset thresholds, the type of QRS complexes already classified within a certain duration, so as to determine the type of arrhythmia.

For example, if five continuous QRS complexes of a type Abnormal have occurred in succession at present, and a current heat rhythm value is greater than 120 bpm, it is determined that the type of arrhythmia indicates ventricular tachycardia. If all determination conditions for arrhythmia are not met, it is determined that a current electrocardiogram signal is of a normal rhythm.

Step 1085, comparing, when the current arrhythmia analysis result of the historical electrocardiogram data indicates an abnormal rhythm, the current arrhythmia analysis result of the historical electrocardiogram data with a historical alarm list to determine whether the historical alarm list contains an alarm prompt about the same type of arrhythmia at a corresponding moment. The flow returns to step 1081 if the historical alarm list contains the alarm prompt about the same type of arrhythmia at the corresponding moment. Step 1086 is carried out if the historical alarm list does not contain the alarm prompt about the same type of arrhythmia at the corresponding moment.

It may be understood that, if the historical alarm list contains the alarm prompt about the same type of arrhythmia at the corresponding moment, which indicates that an alarm prompt about the same type of arrhythmia at the corresponding moment is already output during the process of historical arrhythmia analysis, it is not necessary at present to output a repeated alarm prompt about the same type of arrhythmia at the corresponding moment.

Step 1086, displaying the type and occurrence moment of arrhythmia of the historical electrocardiogram data on a human-machine interaction interface, and outputting an alarm prompt about the type and occurrence moment of arrhythmia.

When the current arrhythmia analysis result of the historical electrocardiogram data indicates an abnormal rhythm, an alarm prompt about the abnormal rhythm and the occurrence moment thereof is output so as to warn the medical personnel, wherein the content of the alarm prompt may comprise the specific type and occurrence moment of arrhythmia.

Figure 9:
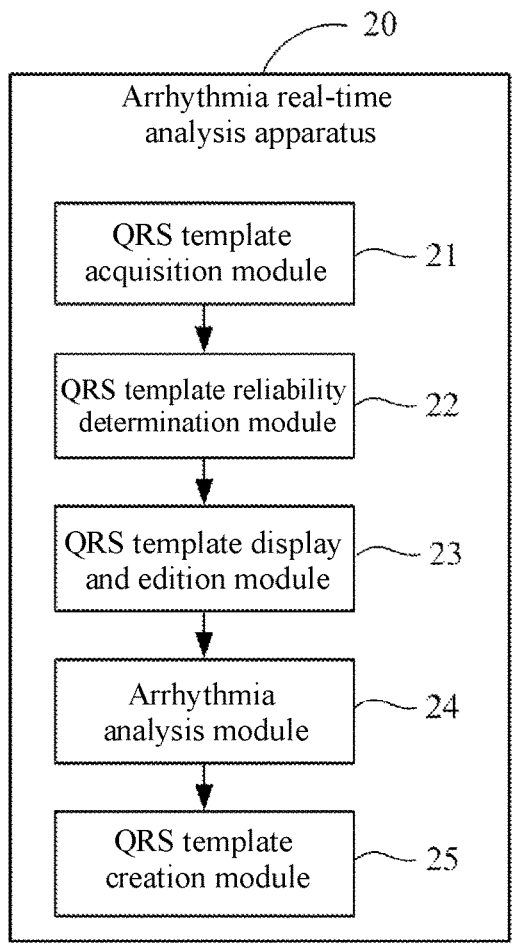
FIG. 9 is a schematic structural diagram of an arrhythmia real-time analysis apparatus provided in an embodiment of the present application.

Referring to FIG. 9, it is a schematic structural diagram of an arrhythmia real-time analysis apparatus 20 provided in an embodiment of the present application. The arrhythmia real-time analysis apparatus 20 is applied to an electrocardiogram monitoring device, such as an electrocardiogram detector. The electrocardiogram monitoring device comprises at least a display screen and an alarm apparatus. The arrhythmia real-time analysis apparatus 20 may comprise one or more modules, the one or more modules being stored in a memory of the electrocardiogram monitoring device and being configured to be carried out by one or more processors (one in this embodiment), so as to complete the present application. For example, with reference to FIG. 9, the arrhythmia real-time analysis apparatus 20 may comprise a QRS template acquisition module 21, a QRS template reliability determination module 22, a QRS template display and edition module 23, an arrhythmia analysis module 24 and a QRS template creation module 25. The module called in this embodiment of the present application may be a program segment for completing a certain function, which is more suitable for describing an execution process of software in the processor than a program. It may be understood that, corresponding to all embodiments of the above-mentioned method for analyzing arrhythmia in real time, the arrhythmia real-time analysis apparatus 20 may comprise some or all of functional modules shown in FIG. 9, and the functions of modules 21 to 25 will be introduced below in detail.

In this embodiment, the QRS template acquisition module 21 is configured to acquire a QRS template set currently used for arrhythmia analysis.

The current QRS template set comprises a plurality of created QRS templates, such as 5 to 6 QRS templates. It may be understood that each QRS template is created from one QRS complex, and the QRS complex may be a QRS complex directly acquired during a process of arrhythmia analysis or a certain QRS complex in historical electrocardiogram data.

Figure 10:
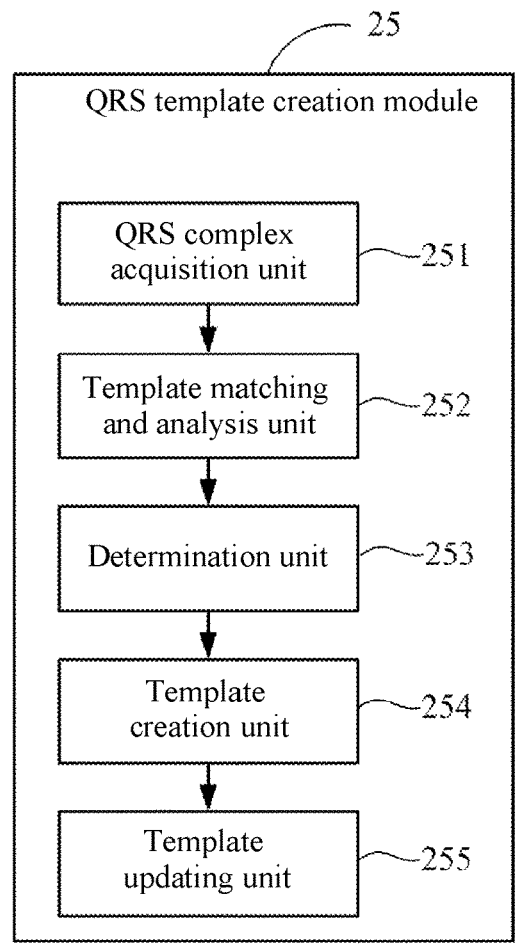
FIG. 10 is a schematic structural diagram of a QRS template creation module in FIG. 1.

In this embodiment, the QRS template creation module 25 is configured to create a QRS template and update the QRS template. With reference to FIG. 10, in this embodiment, the QRS template creation module 25 comprises a QRS complex acquisition unit 251, a template matching unit 252, a determination unit 253, a template creation unit 254, and a template updating unit 255.

The QRS complex acquisition unit 251 is configured to acquire a QRS complex and morphological feature information thereof. The QRS complex may be a QRS complex in real-time electrocardiogram data that is detected during the process of current arrhythmia analysis, or a certain QRS complex in historical electrocardiogram data. The morphological feature information of the QRS complex comprises, but is not limited to, the amplitude, width and slope of the QRS complex.

The template matching unit 252 is configured to match the acquired QRS complex with all QRS templates in the existing QRS template set one by one, and separately calculate a correlation coefficient between the QRS complex and the morphology of each of the QRS templates.

It may be understood that all the QRS templates in the existing QRS template set are classified templates. The template matching unit 252 may be used to match, during matching, the morphological feature information of the QRS complex with feature parameters of all QRS templates in the existing QRS template set, and the feature parameters of the QRS templates comprise, but are not limited to, the width, amplitude and slope of the QRS complex.

The value range of the correlation coefficient may be set arbitrarily. For example, the value range of the correlation coefficient may be set between plus and minus 100, wherein the greater the value is, the higher the similarity is.

It may be understood that the template matching unit 252 is configured to match the acquired QRS complex with all QRS templates in a template library one by one, and separately calculate a correlation coefficient between the QRS complex and the morphology of each existing QRS template.

The determination unit 253 is configured to determine, according to each calculated correlation coefficient, whether a template matching the QRS complex exists in the existing QRS template set.

In this embodiment, a correlation threshold may be preset, for example, to 90. If the calculated correlation coefficient between the QRS complex and one of the QRS templates is greater than 90, it may be considered by the determination unit 253 that the QRS complex matches the QRS template, otherwise, it may be considered that the QRS complex does not match the QRS template.

It may be understood that the determination unit 253 is configured to select a QRS template, which has the maximum correlation coefficient between same and the QRS complex that is greater than the preset correlation threshold, as the optimal matched template for the QRS complex.

The template creation unit 254 is configured to create, if no template matching the QRS complex exists in the existing QRS template set, a new QRS template with morphological feature information of the QRS complex, and determine the type of the new QRS template, wherein the type comprises a type Normal and a type Abnormal.

The template updating unit 255 is configured to update, if a matched template matching the QRS complex exists in the existing QRS template set, feature parameters of the matched template by using the acquired morphological feature information of the QRS complex.

It may be understood that the creation and updating of the QRS template are carried out in real time during the process of arrhythmia analysis, such that more morphological feature information of QRS complexes of the same type may be collected for the feature parameters of the created QRS template, for the determination of the reliability of the QRS template after a certain duration or after the collection of sufficient morphological feature information of the QRS complexes of same type. In addition, a new QRS template may be created for a newly emerging waveform, such that when the same type of waveform is analyzed again, the newly created QRS template may be used to analyze the same type of waveform.

Figure 11:
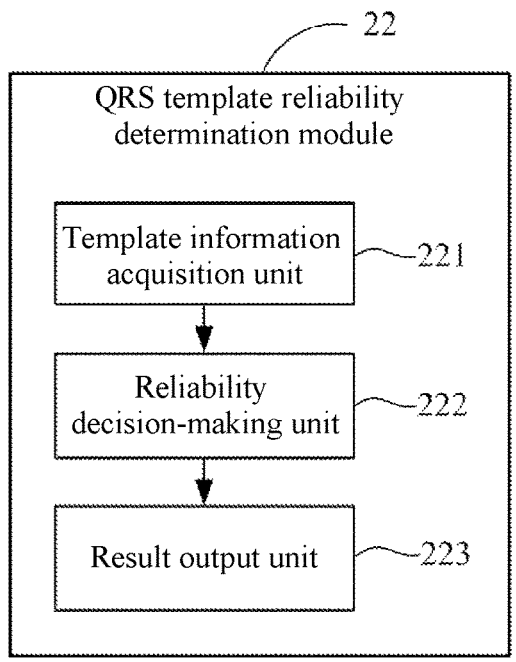
FIG. 11 is a schematic structural diagram of a QRS template reliability determination module in FIG. 1.

In this embodiment, the QRS template reliability determination module 22 is configured to determine whether each QRS template in the current QRS template set is reliable. With reference to FIG. 11, in this embodiment, the QRS template reliability determination module 22 comprises a template information acquisition unit 221, a reliability decision-making unit 222 and a result output unit 223.

The template information acquisition unit 221 is configured to acquire information of each QRS template in the current QRS template set, wherein the information of the QRS template further comprises the type and feature parameters of the QRS template. The feature parameters of the QRS template comprise, but is not limited to, the width, amplitude and slope of a QRS complex, and a start point and an end point of the QRS complex.

The reliability decision-making unit 222 is configured to compare the acquired feature parameters of each QRS template with corresponding preset parameter thresholds, and determine, according to a comparison result, whether each QRS template is reliable.

In one embodiment, it may be determined, depending on whether the feature parameters of the QRS template exceed the corresponding preset parameter thresholds, whether the current template is reliable.

It may be understood that QRS templates of different types also have different feature parameter thresholds.

The parameter thresholds may be set with reference to medically statistical normal values. For example, a QRS template of a type Normal may have a QRS width threshold that is set as 20 ms. A QRS template of a type Abnormal may have a QRS width threshold that is set as 120 ms. In one embodiment, if all or some feature parameters of a template of a certain type exceed the corresponding preset parameter thresholds and meet the corresponding determination conditions, it is determined that the QRS template is unreliable.

The result output unit 223 is configured to output a reliability determination result of each QRS template.

In this embodiment, the QRS template display and edition module 23 is configured to control, when the current QRS template set contains an unreliable QRS template, the display screen to pop up a prompt window for displaying information of a QRS template in the current QRS template set. The information of the QRS template that is displayed in the prompt window comprises a reliability determination result of the QRS template.

In this embodiment, the QRS template display and edition module 23 is further configured to determine the QRS template set according to the operation performed by the user on the information of the QRS template in the current QRS template set that is displayed in the prompt window.

The information of the current QRS template further comprises, but is not limited to, the type of the QRS template and morphological feature parameters of a QRS complex. The morphological feature parameters of the QRS complex comprise, but are not limited to, the amplitude, width and slope of the QRS complex, and a start point and an end point of the QRS complex.

During practical application, as shown in FIG. 2 or 3, the QRS template display and edition module 23 may simultaneously display the information of each currently-created QRS template by means of, but not limited to, a human-machine interaction interface. In this embodiment, the information of only one unreliable QRS template is displayed in both schematic diagrams of FIGS. 2 and 3.

Figure 12:
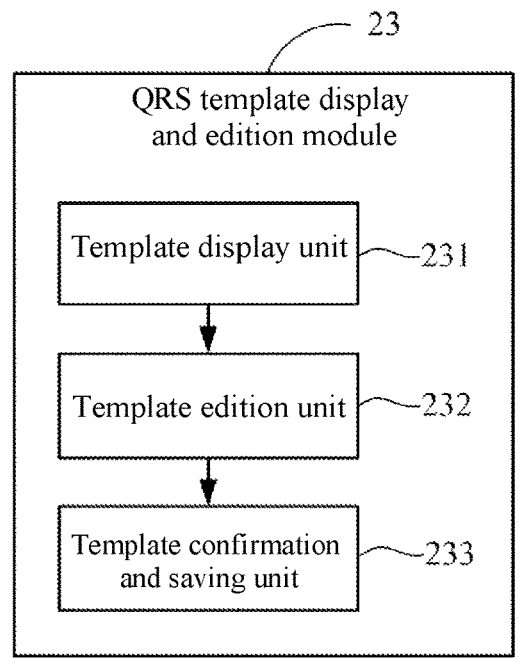
FIG. 12 is a schematic structural diagram of a QRS template display and edition module in FIG. 1.

With reference to FIG. 12, in this embodiment, the QRS template display and edition module 23 comprises a template display unit 231, a template edition unit 232 and a template confirmation and saving unit 233.

The template display unit 231 is configured to control, when the current QRS template set contains an unreliable QRS template, the display screen to pop up a prompt window for displaying information of a QRS template in the current QRS template set.

In one embodiment, the template display unit 231 is configured to pop up two prompt windows on the display screen, for displaying information of a reliable QRS template in one of the prompt windows and information of an unreliable QRS template in the other prompt window, according to the reliability determination result of each QRS template, namely, separately displaying the reliable QRS template and the unreliable QRS template in different prompt windows.

Optionally, in another embodiment, the template display unit 231 is specifically configured to pop up one prompt window on the display screen, for displaying information of an unreliable QRS template in the prompt window according to the reliability determination result of each QRS template.

Optionally, in another embodiment, the template display unit 231 is specifically configured to pop up one prompt window on the display screen, for displaying information of each QRS template in the prompt window, namely, displaying both a reliable QRS template and an unreliable QRS template in the same prompt window.

In this embodiment, when it is determined by the system that all the QRS templates in the current QRS template set are reliable, the prompt window for displaying the information of the QRS template in the current QRS template set is not actively popped up.

The template edition unit 232 is configured to determine the QRS template set according to the operation performed by the user on the information of the QRS template in the current QRS template set that is displayed in the prompt window.

In this embodiment, the reliability determination of a QRS template comprises automatic determination by a machine system and human determination. For example, on the basis of the system automatically determining the reliability of a certain QRS template, the medical personnel may further determine, according to actual clinical conditions and their own experience, whether the QRS template is reliable.

In this embodiment, the operation performed by the user on the information of the QRS template comprises an editing operation and a confirmation operation.

In this embodiment, when determining the QRS template set according to an operation performed by a user on the information of the QRS template, the template edition unit 232 is configured to:

determine a type of the operation performed by the user on the information of the QRS template;

update, if the operation is an editing operation, information of a corresponding QRS template in the QRS template set according to the editing operation; and maintain, if the operation is a confirmation operation, information of a corresponding QRS template in the QRS template set unchanged according to the confirmation operation.

It may be understood that the template display unit 231 may be further configured to display an edition button and a confirmation button in the prompt window, such that the medical personnel may edit or confirm the currently displayed information of the QRS template in the prompt window by means of the edition or confirmation button. The operation performed by the user on the information of the QRS template may be a click operation on the confirmation button or on the edition button and an editing operation for further input following the clicking of the edition button, performed by the user such as the medical personnel in the prompt window.

It may be understood that if it is displayed in the prompt window that the system determines that a certain QRS template is unreliable whereas the medical personnel determines that the QRS template is reliable, that is to say, when considering it unnecessary to perform an editing operation of modifying the QRS template, etc., the medical personnel may confirm information of the QRS template by means of, for example, clicking the confirmation button in the prompt window, so as to maintain the original information of the QRS template unchanged.

In addition, if it is displayed in the prompt window that the system determines that a certain QRS template is unreliable and the medical personnel also determines that the QRS template is unreliable, that is to say, when considering it necessary to perform an editing operation of modifying the QRS template, etc., the medical personnel may edit information of the QRS template by means of, for example, clicking the edition button in the prompt window, so as to modify the information of the QRS template. The content for edition comprises, but is not limited to, modification to the type of the QRS template and morphological feature parameters of the QRS complex, such as parameters of the amplitude, the width and the slope of the QRS complex, and a start point and an end point of the QRS complex.

In other embodiments, the content for edition may further comprise replacement of the QRS template, for example, deleting an original QRS template, and then setting a new QRS template.

The template confirmation and saving unit 233 is configured to save a determined QRS template.

In this embodiment, the arrhythmia analysis module 24 is configured to acquire real-time electrocardiogram data, perform arrhythmia analysis on the real-time electrocardiogram data by using the determined QRS template set, output an arrhythmia analysis result of the real-time electrocardiogram data in real time, and display the arrhythmia analysis result of the real-time electrocardiogram data in real time on the human-machine interaction interface.

Specifically, as shown in FIG. 2, during the process of analyzing arrhythmia in real time, the type of one QRS template P1 in the current template set is a type Normal. If it is determined in step 102 above that the QRS template P1 is unreliable, the medical personnel may modify the type of the QRS template P1 to a type Abnormal in the popped-up prompt window, so as to obtain an edited QRS template P1', and perform arrhythmia analysis on real-time electrocardiogram data D1 by using a QRS template set containing the edited QRS template P1'.

As shown in FIG. 2, when arrhythmia analysis is performed on the real-time electrocardiogram data D1 by using the QRS template P1 before edition, an analysis result indicates no alarm, that is to say, the real-time electrocardiogram data D1 is analyzed to be of a normal rhythm, but in fact, the real-time electrocardiogram data D1 should be of an abnormal rhythm. When arrhythmia analysis is performed on the real-time electrocardiogram data D1 by using the edited QRS template P1', an analysis result obtained indicates a ventricular tachycardia alarm.

It may be understood that under general conditions, creating a QRS template from electrocardiogram waveform parameters, and analyzing the type of arrhythmia by means of a template matching method may meet requirements of real-time analysis of arrhythmia in most cases. But when a special electrocardiogram waveform is encountered or there is a doubt on the type of a current template, for example, when an abnormal electrocardiogram waveform occurs and an arrhythmia analysis result deviates from the actual situation, as described above, each QRS template in the QRS template set may be edited or confirmed so as to reduce the misclassification of QRS complexes and correct the arrhythmia analysis result, thereby improving the accuracy of the real-time analysis result of arrhythmia.

Figure 13:
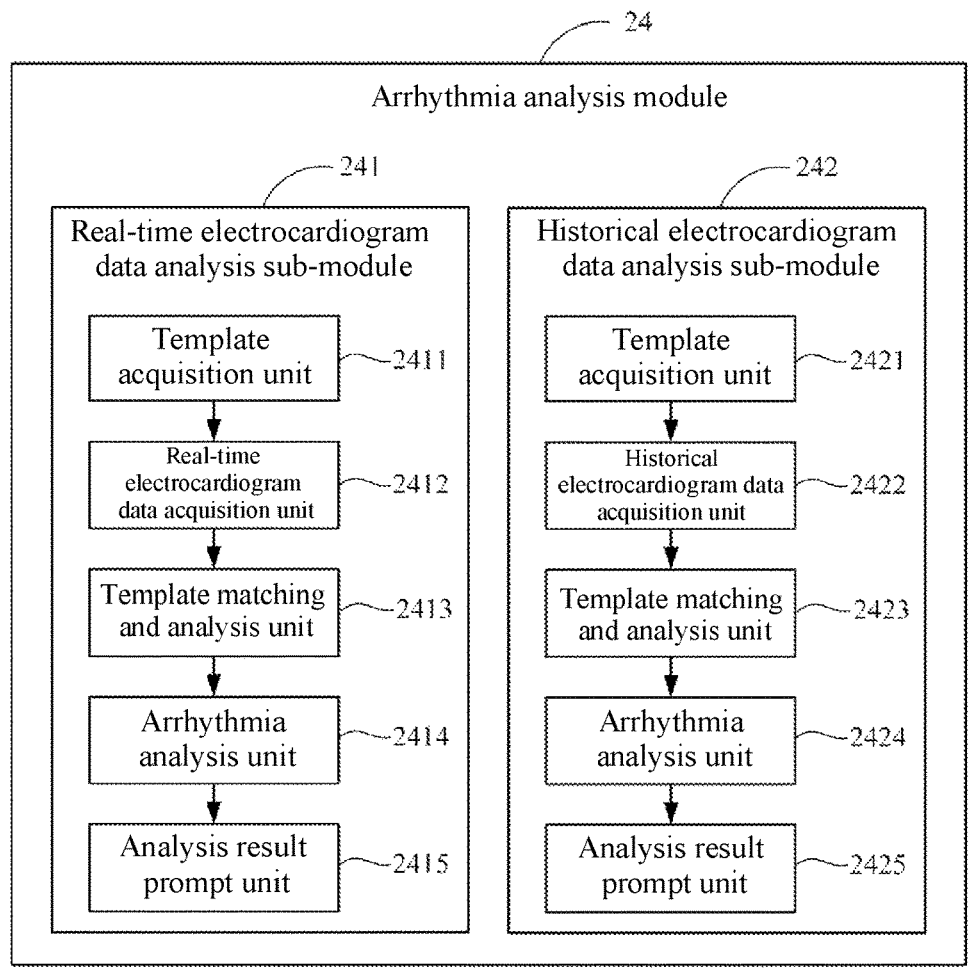
FIG. 13 is a schematic structural diagram of an arrhythmia analysis module in FIG. 1.

With reference to FIG. 13, in this embodiment, the arrhythmia analysis module 24 comprises a real-time electrocardiogram data analysis sub-module 241, and the real-time electrocardiogram data analysis sub-module 241 comprises a template acquisition unit 2411, a real-time electrocardiogram data acquisition unit 2412, a template matching unit 2413, an arrhythmia analysis unit 2414 and an analysis result prompt unit 2415.

The template acquisition unit 2411 is configured to acquire a determined QRS template set.

The real-time electrocardiogram data acquisition unit 2412 is configured to acquire real-time electrocardiogram data to be analyzed.

The template matching unit 2413 is configured to match QRS complexes in the real-time electrocardiogram data with all QRS templates contained in the determined QRS template set one by one, and classify the QRS complexes in the real-time electrocardiogram data according to a matching result.

In this embodiment, the template matching unit 2413 is configured to:

match the QRS complex in the real-time electrocardiogram data with all the QRS templates contained in the determined QRS template set one by one, and calculate a correlation coefficient between the QRS complex and the morphology of each of the QRS templates contained in the determined QRS template set; and determine, when there is a maximum correlation coefficient between the QRS complex and one of the QRS templates and the maximum correlation coefficient is greater than a preset correlation threshold, that the QRS complex matches the one of the QRS templates, and determine the type of the QRS complex according to the type of the one of the QRS templates, that is to say, classifying the QRS complex as the type of the one of the QRS templates.

The arrhythmia analysis unit 2414 is configured to analyze the type of arrhythmia according to a classification result of the QRS complexes, and output an arrhythmia analysis result of the real-time electrocardiogram data.

In this embodiment, the arrhythmia analysis unit 2414 is configured to analyze, in combination with specific arrhythmia determination criteria and/or preset thresholds, the type of QRS complexes already classified within a certain duration, so as to determine the type of arrhythmia.

For example, if five continuous QRS complexes of a type Abnormal have occurred in succession at present, and a current heat rhythm value is greater than 120 bpm, it is determined that the type of arrhythmia indicates ventricular tachycardia. If all determination conditions for arrhythmia are not met, it is determined that a current electrocardiogram signal is of a normal rhythm.

The analysis result prompt unit 2415 is configured to control the display screen to display the human-machine interaction interface, and display the arrhythmia analysis result, such as the type of arrhythmia, of the real-time electrocardiogram data in real time on the human-machine interaction interface.

In this embodiment, the analysis result prompt unit 2415 is further configured to control, when the arrhythmia analysis result of the real-time electrocardiogram data indicates an abnormal rhythm, the alarm apparatus to output a real-time alarm prompt about the abnormal rhythm.

When the current arrhythmia analysis result of the real-time electrocardiogram data indicates an abnormal rhythm, a real-time alarm prompt about the abnormal rhythm is output to warn the medical personnel, wherein the content of the alarm prompt may comprise the specific type of arrhythmia.

An inaccurate template may cause serious arrhythmia reflected in historical electrocardiogram data of a patient not to be recognized, which further has an effect on determination of the patient's condition by the medical personnel, thereby increasing medical risks, and lowering the quality of electrocardiogram monitoring.

In this embodiment, when each QRS template in the current QRS template set is reliable, the real-time electrocardiogram data analysis sub-module 241 is configured to perform arrhythmia analysis on the real-time electrocardiogram data by using the current QRS template set, and output an arrhythmia analysis result of the real-time electrocardiogram data in real time.

As described above, when it is determined by the system that all the QRS templates in the current QRS template set are reliable, the prompt window for displaying the information of the QRS template in the current QRS template set is not actively popped up. In addition, on the basis of the system automatically determining the reliability of a certain QRS template, the medical personnel may further determine, according to actual clinical conditions and their own experience, whether the QRS template is reliable.

In this embodiment, the template display unit 231 is further configured to receive a call operation input on the human-machine interaction interface, and call, according to the received call operation, the prompt window for displaying the information of the QRS template in the current QRS template set.

For example, during the analysis of a special electrocardiogram waveform, if determining, according to actual clinical conditions and their own experience, that the result of arrhythmia analysis with the currently created QRS template deviates from the actual situation, the medical personnel may click a relevant button on the human-machine interaction interface in real time to actively display the currently created QRS template, namely, calling the prompt window for displaying the information of the QRS template in the current QRS template set.

It may be understood that the medical personnel may further input, at any moment during the process of arrhythmia analysis, a call operation on the human-machine interaction interface to call the information of the QRS template in the current QRS template set, so as to determine whether the QRS template is reliable.

If determining that a certain QRS template is reliable, the medical personnel may input a confirmation operation in the prompt window so as to maintain the original information of the QRS template unchanged. In addition, if determining that the QRS template is unreliable, the medical personnel may input an editing operation in the prompt window so as to modify information of the QRS template, such as modifying the type, amplitude, width and slope of the QRS template, a start point and an end point of a QRS complex, etc.

In this embodiment, the arrhythmia analysis module 24 is further configured to acquire historical electrocardiogram data after the current QRS template set is edited, perform arrhythmia analysis again on the historical electrocardiogram data by using the edited QRS template, and output an arrhythmia analysis result of the historical electrocardiogram data.

Specifically, as shown in FIG. 3, during the process of analyzing arrhythmia in real time, for example, by way of taking a moment T as a real-time analysis time point, the type of one QRS template P2 in the current template set is a type Normal. If it is determined in step 102 above that the QRS template P2 is unreliable, the medical personnel may modify the type of the template P2 to a type Abnormal in the popped-up prompt window, so as to obtain an edited QRS template P2', and perform arrhythmia analysis again on the historical electrocardiogram data D2 by using a QRS template set containing the edited QRS template P2'.

As shown in FIG. 3, a historical arrhythmia analysis result of the historical electrocardiogram data D2 indicates no alarm, that is to say, during the process of historical arrhythmia analysis, the historical electrocardiogram data D2 is analyzed to be of a normal rhythm, but in fact, the historical electrocardiogram data D2 should be of an abnormal rhythm. After arrhythmia analysis is performed again on the historical electrocardiogram data D2 by using the edited QRS template P2', a reanalysis result obtained indicates a ventricular tachycardia alarm.

In this way, the historical electrocardiogram data is reanalyzed by using the edited QRS template, such that omission of serious arrhythmia reflected in the historical electrocardiogram data of the patient may be avoided, and alarm omissions may be reduced, thereby improving the accuracy of arrhythmia analysis and then improving the quality of electrocardiogram monitoring.

In this embodiment, the arrhythmia analysis module 24 further comprises a historical electrocardiogram data analysis sub-module 242, and the historical electrocardiogram data analysis sub-module 242 comprises a template acquisition unit 2421, a historical electrocardiogram data acquisition unit 2422, a template matching unit 2423, an arrhythmia analysis unit 2424 and an analysis result prompt unit 2425.

The template acquisition unit 2421 is configured to acquire all the edited QRS templates.

The historical electrocardiogram data acquisition unit 2422 is configured to acquire historical electrocardiogram data to be reanalyzed.

The template matching unit 2423 is configured to match QRS complexes in the historical electrocardiogram data with all the edited QRS templates one by one, and classify the QRS complexes in the historical electrocardiogram data according to a matching result.

In this embodiment, the template matching unit 2423 is configured to:

match the QRS complex in the historical electrocardiogram data with all the edited QRS templates one by one, and calculate a correlation coefficient between the QRS complex and the morphology of each of the edited QRS templates; and determine, when there is a maximum correlation coefficient between the QRS complex and one of the QRS templates and the maximum correlation coefficient is greater than a preset correlation threshold, that the QRS complex matches the one of the QRS templates, and determine the type of the QRS complex according to the type of the one of the QRS templates, that is to say, classifying the QRS complex as the type of the one of the QRS templates.

The arrhythmia analysis unit 2424 is configured to analyze the type of arrhythmia according to a classification result of the QRS complexes, and output a current arrhythmia analysis result of the historical electrocardiogram data and record the occurrence moment of arrhythmia.

In this embodiment, the arrhythmia analysis unit 2424 is configured to analyze, in combination with specific arrhythmia determination criteria and/or preset thresholds, the type of QRS complexes already classified within a certain duration, so as to determine the type of arrhythmia.

For example, if five continuous QRS complexes of a type Abnormal have occurred in succession at present, and a current heat rhythm value is greater than 120 bpm, it is determined that the type of arrhythmia indicates ventricular tachycardia. If all determination conditions for arrhythmia are not met, it is determined that a current electrocardiogram signal is of a normal rhythm.

The analysis result prompt unit 2425 is configured to compare, when the current arrhythmia analysis result of the historical electrocardiogram data indicates an abnormal rhythm, the current arrhythmia analysis result of the historical electrocardiogram data with a historical alarm list to determine whether the historical alarm list contains an alarm prompt about the same type of arrhythmia at a corresponding moment; and the analysis result prompt unit is configured to control, when the historical alarm list does not contain the alarm prompt about the same type of arrhythmia at the corresponding moment, the display screen to display a human-machine interaction interface, displaying the type and occurrence moment of arrhythmia of the historical electrocardiogram data on a human-machine interaction interface, and controlling the alarm apparatus to output an alarm prompt about the type and occurrence moment of arrhythmia.

When the current arrhythmia analysis result of the historical electrocardiogram data indicates an abnormal rhythm, an alarm prompt about the abnormal rhythm and the occurrence moment thereof is output so as to warn the medical personnel, wherein the content of the alarm prompt may comprise the specific type and occurrence moment of arrhythmia.

It may be understood that, if the historical alarm list contains the alarm prompt about the same type of arrhythmia at the corresponding moment, which indicates that an alarm prompt about the same type of arrhythmia at the corresponding moment is already output during the process of historical arrhythmia analysis, it is not necessary at present to output a repeated alarm prompt about the same type of arrhythmia at the corresponding moment.

The arrhythmia real-time analysis apparatus in the present invention may achieve the correction of a template of a special waveform by means of editing a currently created QRS template; when the same type of waveform is analyzed again, a correct arrhythmia analysis result may be provided. Meanwhile, the historical electrocardiogram data is reanalyzed by using the edited QRS template, such that omission of serious arrhythmia reflected in the historical electrocardiogram data of the patient may be avoided, and alarm omissions may be reduced, thereby improving the accuracy of arrhythmia analysis and then improving the quality of electrocardiogram monitoring.

An embodiment of the present application further provides an electrocardiogram monitoring device, which comprises a memory, a processor, and a computer program stored on the memory and operable on the processor, wherein the processor implements, when executing the program, the steps of the method for analyzing arrhythmia in real time in the above-mentioned embodiment.

Figure 14:
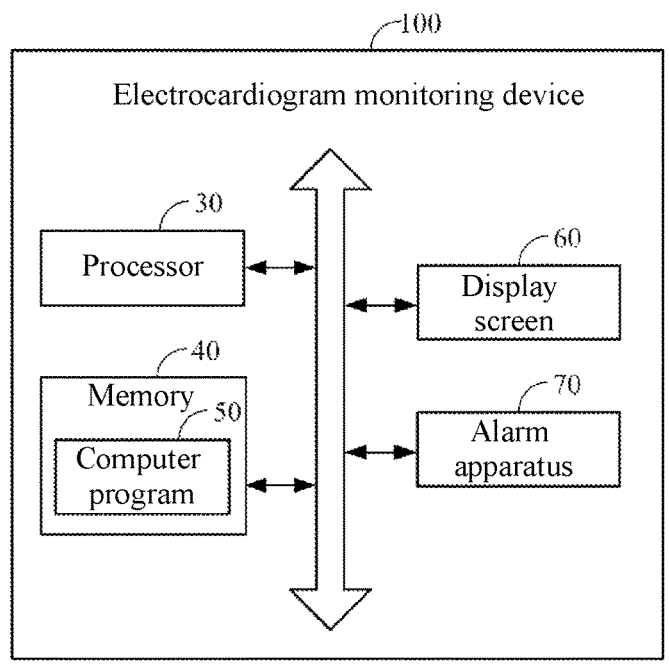
FIG. 14 is a schematic structural diagram of an electrocardiogram monitoring device provided in an embodiment of the present application.

FIG. 14 is a schematic structural diagram of an electrocardiogram monitoring device 100 provided in an embodiment of the present application. As shown in FIG. 14, the electrocardiogram monitoring device 100 comprises at least a processor 30, a memory 40, a computer program 50 (such as an arrhythmia real-time analysis program) stored in the memory 40 and operable on the processor 30, a display screen 60 and an alarm apparatus 70.

The electrocardiogram monitoring device 100 may be, for example, an electrocardiogram detector. Those skilled in the art may understand that schematic diagram 14 is merely an example of the electrocardiogram monitoring device 100 for implementing the method for analyzing arrhythmia in real time in the present application, and does not constitute a limitation on the electrocardiogram monitoring device 100. More or fewer components than shown may be comprised, or some components may be combined, or different components may be comprised. For example, the electrocardiogram monitoring device 100 may further comprise an input and output device, a network access device, etc. The display screen 60 may be configured to provide a human-machine interaction interface to display data which is output according to the use of the electrocardiogram monitoring device 100, for example, to display information of the above current QRS template and a reliability determination result thereof, to display the type of arrhythmia of the above real-time electrocardiogram data in real time, to display the type and occurrence moment of arrhythmia of the above historical electrocardiogram data, etc.

The alarm apparatus 70 may be configured to provide audio to output a prompt about the data which is output according to the use of the electrocardiogram monitoring device 100, for example, to output a real-time alarm prompt about the abnormal rhythm, to output a real-time alarm prompt about the type and occurrence moment of arrhythmia, etc. The alarm apparatus 70 may be a buzzer, a loudspeaker, etc.

The processor 30 implements, when executing the computer program 50, the steps in each above-mentioned embodiment of the method for analyzing arrhythmia in real time, such as steps 101 to 111 shown in FIG. 1, or steps 121 to 127 shown in FIG. 4, or steps 201 to 205 shown in FIG. 5, or steps 1021 to 1023 shown in FIG. 6, or steps 1061 to 1064 shown in FIG. 7, or steps 1081 to 1086 shown in FIG. 8. Alternatively, the processor 30 implements, when executing the computer program 50, the functions of modules/units, such as modules 21 to 25, in the above-mentioned embodiment of the arrhythmia real-time analysis apparatus 20.

Exemplarily, the computer program 50 may be divided into one or more modules/units, wherein the one or more modules/units are stored in the memory 40 and are executed by the processor 30 to complete the present application. The one or more modules/units may be a series of instruction segments of computer program 50 that can implement specific functions, wherein the instruction segments are used to describe an execution process of the computer program 50 in the electrocardiogram monitoring device 100. For example, the computer program 50 may be divided into the QRS template acquisition module 21, the QRS template reliability determination module 22, the QRS template display and edition module 23, the arrhythmia analysis module 24 and the QRS template creation module 25 in FIG. 9. The specific functions of modules 21 to 25 refer to the detailed instruction above, which will not be described here again for the sake of saving space and avoiding repetition.

The called processor 30 may be a central processing unit (CPU) or other general-purpose processors, a digital signal processor (DSP), an application specific integrated circuit (ASIC), a field-programmable gate array (FPGA), or other programmable logic devices, a discrete gate or transistor logic device, a discrete hardware component, etc. The general-purpose processor may be a microprocessor, or the processor may be any conventional processor, etc. The processor 30 is a control center of the electrocardiogram monitoring device 100, and is used to connect all parts of the whole arrhythmia real-time analysis apparatus 20/electrocardiogram monitoring device 100 by means of various interfaces and lines.

The memory 40 may be configured to store the computer program 50 and/or the modules/units, and the processor 30 is configured to implement various functions of the arrhythmia real-time analysis apparatus 20/electrocardiogram monitoring device 100 by means of running or executing the computer program 50 and/or the modules/units stored in the memory 40, and calling data stored in the memory 40. The memory 40 may mainly comprise a program storage area and a data storage area, wherein the program storage area may be used to store an operating system, application programs required for at least one function (for example, a sound playback function, and an image display function), etc; and the data storage area may be used to store data (for example, audio data, a phone book, and data set and acquired by using the above method for analyzing arrhythmia in real time), etc. that is created according to usage of the electrocardiogram monitoring device 100. In addition, the memory 40 may comprise a high-speed random access memory, and may further comprise a non-volatile memory such as a hard disk, an internal memory, and a removable hard disk, a smart media card (SMC), a secure digital (SD) card, a flash card, at least one disk storage device, a flash storage device or another volatile solid-state storage device.

The present application further provides a computer-readable storage medium having a computer program stored thereon, wherein the computer program implements, when executed by a processor, the steps of the method for analyzing arrhythmia in real time in the above-mentioned embodiments.

The module/unit integrated in the arrhythmia real-time analysis apparatus 20/the electrocardiogram monitoring device 100/a computer apparatus of the present application may be stored in one computer-readable storage medium if implemented in the form of a software functional unit and sold or used as an independent product. Based on such an understanding, all or some procedures in the methods in the embodiments implemented in the present application may be accomplished by a computer program instructing related hardware. The computer program may be stored in one computer-readable storage medium, and when executed by a processor, the computer program may implement the steps in the method embodiments above. The computer program comprises computer program codes, which may be in the form of source codes, object codes, an executable file or some intermediate forms, etc. The computer-readable medium may comprise: any entity or apparatus capable of carrying the computer program code, a recording medium, a USB flash drive, a mobile hard disk drive, a magnetic disk, an optical disk, a computer memory, a read-only memory (ROM), a random access memory (RANI), an electrical carrier signal, a telecommunication signal, a software distribution medium, etc. It should be noted that appropriate additions or deletions may be made to the content comprised in the computer-readable medium according to the requirements of the legislation in a jurisdictional area and patent practice. For example, in some jurisdictional areas, according to the legislation and patent practice, the computer-readable medium does not comprise an electrical carrier signal or a telecommunication signal.

It should be understood that in several specific embodiments provided in the present application, the disclosed method and apparatus for analyzing arrhythmia in real time may be implemented in other ways. For example, the embodiment of the arrhythmia real-time analysis apparatus described above is merely exemplary. For example, the division of modules is merely a kind of logic function division, and there may be other division modes in actual implementation.

In addition, the functional modules in the embodiments of the present application may be integrated into the same processing module, or each module may be physically present separately, or two or more modules may be integrated into the same module. The above integrated modules may be implemented in the form of hardware, or may be implemented in the form of hardware plus a software functional module.

For those skilled in the art, it is apparent that the present application is not limited to the details of the above-mentioned exemplary embodiments, and the present application can be implemented in other specific forms without departing from the spirit or basic features of the present application. Therefore, no matter from which point of view, the embodiments should all be regarded as exemplary and non-limiting. The scope of the present application is defined by the appended claims rather than the above-mentioned description, and therefore it is intended that all changes which fall within the meaning and scope of equivalency of the claims are embraced in the present application. Any reference numeral in the claims should not be construed as limiting the related claims. In addition, it is apparent that the word "comprise 包括)" does not exclude other units or steps, and the singular does not exclude the plural. A plurality of units or apparatuses stated in the device claims may also be implemented by the same one unit or apparatus by means of software or hardware.

Finally, it should be noted that the above-mentioned embodiments are merely intended for describing the technical solutions of the present application rather than limiting the present application. Although the present application is described in detail with reference to the above-mentioned embodiments, persons of ordinary skill in the art should understand that they may still make modifications or equivalent replacements to the technical solutions of the present application without departing from the spirit and scope of the technical solutions of the present application.

The invention claimed is:

1. A method for analyzing arrhythmia in real time, comprising:
    acquiring a QRS template set currently used for arrhythmia analysis, wherein the current QRS template set comprises a plurality of QRS templates;
    determining whether each QRS template in the current QRS template set is reliable, comprising comparing feature parameters of each QRS template with corresponding preset parameter thresholds to obtain a comparison result and determining, according to the comparison result, whether each QRS template is reliable;
    in response to the current QRS template set containing an unreliable QRS template, displaying information of the QRS template, wherein the information of the QRS template comprises a reliability determination result of the QRS template, and displaying the information of the QRS template comprises popping up one or more prompt windows to display the information of the QRS template;

determining a QRS template set as a determined QRS template set according to an operation performed by a user on the information of the current QRS template; and acquiring real-time electrocardiogram data, performing arrhythmia analysis on the real-time electrocardiogram data by using the determined QRS template set, and outputting an arrhythmia analysis result of the electrocardiogram data in real time.

2. The method for analyzing arrhythmia in real time of claim 1, further comprising:

receiving a call operation when each QRS template in the current QRS template set is reliable, and calling the information of the QRS template according to the received call operation;

determining the current QRS template set according to the operation performed by the user on the information of the QRS template; and acquiring the real-time electrocardiogram data, performing the arrhythmia analysis on the real-time electrocardiogram data by using the current QRS template set, and outputting the arrhythmia analysis result of the real-time electrocardiogram data in real time.

3. The method for analyzing arrhythmia in real time of claim 2, wherein acquiring the real-time electrocardiogram data, performing the arrhythmia analysis on the real-time electrocardiogram data by using the determined QRS template set, and outputting the arrhythmia analysis result of the real-time electrocardiogram data in real time, comprise:

acquiring the determined QRS template set;

acquiring the real-time electrocardiogram data to be analyzed;

matching QRS complexes in the real-time electrocardiogram data with each of the QRS templates contained in the determined QRS template set, and classifying the QRS complexes in the real-time electrocardiogram data according to a matching result; and analyzing a type of arrhythmia according to a classification result of the QRS complexes, and outputting the arrhythmia analysis result of the real-time electrocardiogram data.

4. The method for analyzing arrhythmia in real time of claim 3, wherein matching the QRS complexes in the real-time electrocardiogram data with each of the QRS templates contained in the determined QRS template set, and classifying the QRS complexes in the real-time electrocardiogram data according to the matching result, comprise:

matching the QRS complex in the real-time electrocardiogram data with each of the QRS templates contained in the determined QRS template set, and calculating a correlation coefficient between a QRS complex and morphology of each of the QRS templates contained in the determined QRS template set; and when there is a maximum correlation coefficient between the QRS complex and one of the QRS templates and the maximum correlation coefficient is greater than a preset correlation threshold, determining that the QRS complex matches the one of the QRS templates, and determining the type of the QRS complex according to the type of the one of the QRS templates.

5. The method for analyzing arrhythmia in real time of claim 3, wherein analyzing the type of arrhythmia according to the classification result of the QRS complexes comprises:

analyzing, in combination with arrhythmia determination criteria and/or preset thresholds, the type of QRS complexes that have been already classified within a certain duration, so as to determine the type of arrhythmia.

6. The method for analyzing arrhythmia in real time of claim 1, wherein the operation performed by the user on the information of the QRS template comprises an editing operation, and the method for analyzing arrhythmia in real time further comprises:

after the current QRS template set is edited, acquiring historical electrocardiogram data, performing arrhythmia analysis on the historical electrocardiogram data by using the edited QRS template set, and outputting an arrhythmia analysis result of the historical electrocardiogram data.

7. The method for analyzing arrhythmia in real time of claim 6, wherein acquiring the historical electrocardiogram data, performing the arrhythmia analysis on the historical electrocardiogram data by using the edited QRS template, and outputting the arrhythmia analysis result of the historical electrocardiogram data, comprise:

acquiring all the edited QRS templates;

acquiring the historical electrocardiogram data to be reanalyzed;

matching QRS complexes in the historical electrocardiogram data with each of the edited QRS templates, and classifying the QRS complexes in the historical electrocardiogram data according to a matching result; and analyzing a type of arrhythmia according to a classification result of the QRS complexes, outputting the arrhythmia analysis result of the historical electrocardiogram data and recording an occurrence moment of arrhythmia.

8. The method for analyzing arrhythmia in real time of claim 7, further comprising:

when the current arrhythmia analysis result of the historical electrocardiogram data indicates an abnormal rhythm, comparing the current arrhythmia analysis result of the historical electrocardiogram data with a historical alarm list, to determine whether the historical alarm list contains an alarm prompt about a same type of arrhythmia at a corresponding moment; and when the historical alarm list does not contain an alarm prompt about the same type of arrhythmia at a corresponding moment, displaying the type and occurrence moment of arrhythmia of the historical electrocardiogram data on a human-machine interaction interface, and outputting an alarm prompt about the type and occurrence moment of arrhythmia.

9. The method for analyzing arrhythmia in real time of claim 1, wherein determining whether each QRS template in the current QRS template set is reliable further comprises:

acquiring information of each QRS template in the current QRS template set, wherein the information of the QRS template comprises type information and the feature parameters of the QRS template; and outputting a reliability determination result of each QRS template.

10. The method for analyzing arrhythmia in real time of claim 1, wherein displaying the information of the QRS template comprises:

popping up two first prompt windows, and displaying information of a reliable QRS template in one of the first prompt windows and information of an unreliable QRS template in another one of the first prompt windows, according to the reliability determination result of each QRS template; or popping up a second prompt window, and displaying the information of the unreliable QRS template in the second prompt window according to the reliability determination result of each QRS template; or popping up a third prompt window, and displaying information of each QRS template in the third prompt window, according to the reliability determination result of each QRS template.

11. The method for analyzing arrhythmia in real time of claim 1, further comprising:
   acquiring a QRS complex and morphological feature information corresponding to the QRS complex;
   matching the acquired QRS complex and each of the QRS templates in the current QRS template set, and respectively calculating a correlation coefficient between the QRS complex and the morphology of each of the QRS templates;
   determining, according to each calculated correlation coefficient, whether a template that matches the QRS complex exists in the current QRS template set;
   creating, when the template that matches the QRS complex doesn't exist in the current QRS template set, a new QRS template with the morphological feature information of the QRS complex, and determining a type of the new QRS template; and
   updating, when a matched template matching the QRS complex exists in the current QRS template set, feature parameters of the matched template by using the acquired morphological feature information of the QRS complex.

12. The method for analyzing arrhythmia in real time of claim 1, wherein determining the QRS template set according to the operation performed by the user on the information of the QRS template comprises:
   determining a type of the operation performed by the user on the information of the QRS template;
   updating, when the operation is an editing operation, information of a corresponding QRS template in the QRS template set according to the editing operation; and
   maintaining, when the operation is a confirmation operation, information of a corresponding QRS template in the QRS template set unchanged according to the confirmation operation.

13. An electrocardiogram monitoring device, comprising a display screen, a processor, a memory, and a computer program stored in the memory, wherein the processor is configured to execute the computer program stored in the memory to perform:
   acquiring a QRS template set currently used for arrhythmia analysis, wherein the current QRS template set comprises a plurality of QRS templates;
   determining whether each QRS template in the current QRS template set is reliable, comprising comparing feature parameters of each QRS template with corresponding preset parameter thresholds to obtain a comparison result and determining, according to the comparison result, whether each QRS template is reliable;
   in response to the current QRS template set containing an unreliable QRS template, controlling the display screen to display information of the QRS template, wherein the information of the QRS template comprises a reliability determination result of the QRS template, and the processor is further configured to execute the computer program to control the display screen to pop up one or more prompt windows to display the information of the QRS template;
   determining a QRS template set to be a determined QRS template set according to an operation performed by a user on the information of the QRS template; and
   acquiring real-time electrocardiogram data, performing arrhythmia analysis on the real-time electrocardiogram data by using the determined QRS template set, and outputting an arrhythmia analysis result of the real-time electrocardiogram data in real time.

14. The electrocardiogram monitoring device of claim 13, wherein the processor is further configured to execute the computer program stored in the memory to perform:
   receiving a call operation when each QRS template in the current QRS template set is reliable, and calling the information of the QRS template according to the received call operation;
   determining the current QRS template set according to the operation performed by the user on the information of the QRS template; and
   acquiring the real-time electrocardiogram data, performing the arrhythmia analysis on the real-time electrocardiogram data by using the determined QRS template set, and outputting the arrhythmia analysis result of the real-time electrocardiogram data in real time.

15. The electrocardiogram monitoring device of claim 14, wherein the electrocardiogram monitoring device further comprises an alarm apparatus, and the processor executes the computer program stored in the memory to perform:
   acquiring the determined QRS template set;
   acquiring the real-time electrocardiogram data to be analyzed;
   matching QRS complexes in the real-time electrocardiogram data with each of the QRS templates contained in the determined QRS template set one by one, and classifying the QRS complexes in the real-time electrocardiogram data according to a matching result; and
   analyzing a type of arrhythmia according to a classification result of the QRS complexes, and outputting the arrhythmia analysis result of the real-time electrocardiogram data.

16. The electrocardiogram monitoring device of claim 13, wherein the electrocardiogram monitoring device further comprises an alarm apparatus, and the processor is further configured to execute the computer program stored in the memory to perform:
   controlling the display screen to display a human-machine interaction interface;
   displaying the arrhythmia analysis result of the real-time electrocardiogram data in real time on the human-machine interaction interface; and
   when the arrhythmia analysis result of the real-time electrocardiogram data indicates an abnormal rhythm, controlling the alarm apparatus to output a real-time alarm prompt about the abnormal rhythm.

17. The electrocardiogram monitoring device of claim 13, wherein the operation performed by the user on the information of the QRS template comprises an editing operation, and the processor is further configured to execute the computer program stored in the memory to perform:
   after the information of the QRS template in the current QRS template set is edited, acquiring historical electrocardiogram data, performing arrhythmia analysis on the historical electrocardiogram data by using the edited QRS template, and outputting an arrhythmia analysis result of the historical electrocardiogram data.

18. The electrocardiogram monitoring device of claim 17, wherein the processor executes the computer program stored in the memory to perform:

acquiring all the edited QRS templates;
acquiring the historical electrocardiogram data to be reanalyzed;
matching QRS complexes in the historical electrocardiogram data with each of the edited QRS templates, and classifying the QRS complexes in the historical electrocardiogram data according to a matching result; and
analyzing a type of arrhythmia according to a classification result of the QRS complexes, outputting a current arrhythmia analysis result of the historical electrocardiogram data and recording an occurrence moment of arrhythmia.

19. The electrocardiogram monitoring device of claim 18, wherein the processor is further configured to execute the computer program stored in the memory to perform:
when the current arrhythmia analysis result of the historical electrocardiogram data indicates an abnormal rhythm, comparing the current arrhythmia analysis result of the historical electrocardiogram data with a historical alarm list to determine whether the historical alarm list contains an alarm prompt about the same type of arrhythmia at a corresponding moment; and
when the historical alarm list does not contain an alarm prompt about the same type of arrhythmia at a corresponding moment, controlling the display screen to display a human-machine interaction interface, displaying the type and occurrence moment of arrhythmia of the historical electrocardiogram data on the human-machine interaction interface, and controlling an alarm apparatus to output an alarm prompt about the type and occurrence moment of arrhythmia.

20. The electrocardiogram monitoring device of claim 13, wherein the processor executes the computer program stored in the memory to determine the QRS template set according to the operation performed by the user on the information of the QRS template by performing:
determining a type of the operation performed by the user on the information of the QRS template;
updating, when the operation is an editing operation, information of a corresponding QRS template in the QRS template set according to the editing operation; and
maintaining, when the operation is a confirmation operation, information of a corresponding QRS template in the QRS template set unchanged according to the confirmation operation.

21. A method for analyzing arrhythmia in real time, comprising:
acquiring a QRS template set currently used for arrhythmia analysis, wherein the current QRS template set comprises a plurality of QRS templates;
determining whether each QRS template in the current QRS template set is reliable;
receiving a call operation when each QRS template in the current QRS template set is reliable, and calling information of the QRS template according to the received call operation;
when the current QRS template set contains an unreliable QRS template, displaying the information of the QRS template, wherein the information of the QRS template comprises a reliability determination result of the QRS template;
determining a QRS template set to be a determined QRS template set according to an operation performed by a user on the information of the current QRS template; and
acquiring real-time electrocardiogram data, performing arrhythmia analysis on the real-time electrocardiogram data by using the determined QRS template set, and outputting an arrhythmia analysis result of the electrocardiogram data in real time.

22. A method for analyzing arrhythmia in real time, comprising:
acquiring a QRS template set currently used for arrhythmia analysis, wherein the current QRS template set comprises a plurality of QRS templates;
determining whether each QRS template in the current QRS template set is reliable;
when the current QRS template set contains an unreliable QRS template, displaying information of the QRS template, wherein the information of the QRS template comprises a reliability determination result of the QRS template, and displaying the information of the QRS template comprises:
popping up two first prompt windows, and displaying information of a reliable QRS template in one of the first prompt windows and information of the unreliable QRS template in another one of the first prompt windows, according to the reliability determination result of each QRS template; or
popping up a second prompt window, and displaying the information of the unreliable QRS template in the second prompt window according to the reliability determination result of each QRS template; or
popping up a third prompt window, and displaying information of each QRS template in the third prompt window;
determining a QRS template set to be a determined QRS template set according to an operation performed by a user on the information of the current QRS template; and
acquiring real-time electrocardiogram data, performing arrhythmia analysis on the real-time electrocardiogram data by using the determined QRS template set, and outputting an arrhythmia analysis result of the electrocardiogram data in real time.

23. An electrocardiogram monitoring device, comprising a display screen, a processor, a memory, and a computer program stored in the memory, wherein the processor is configured to execute the computer program stored in the memory to perform:
acquiring a QRS template set currently used for arrhythmia analysis, wherein the current QRS template set comprises a plurality of QRS templates;
determining whether each QRS template in the current QRS template set is reliable;
receiving a call operation when each QRS template in the current QRS template set is reliable, and calling information of the QRS template according to the received call operation;
when the current QRS template set contains an unreliable QRS template, controlling the display screen to display the information of the QRS template, wherein the information of the QRS template comprises a reliability determination result of the QRS template;
determining a QRS template set to be a determined QRS template according to an operation performed by a user on the information of the QRS template; and
acquiring real-time electrocardiogram data, performing arrhythmia analysis on the real-time electrocardiogram data by using the determined QRS template set, and outputting an arrhythmia analysis result of the real-time electrocardiogram data in real time.

* * * * *